(12) United States Patent
Degenhardt et al.

(10) Patent No.: US 7,018,642 B2
(45) Date of Patent: Mar. 28, 2006

(54) COMPOUNDS, COMPOSITIONS, AND METHODS FOR CONTROLLING BIOFILMS

(75) Inventors: Charles Raymond Degenhardt, Cincinnati, OH (US); Rowan Andrew Grayling, Loveland, OH (US); Christopher Andrew Dille, Erlanger, KY (US); Cheryl Sue Tansky, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 166 days.

(21) Appl. No.: 10/132,906

(22) Filed: Apr. 25, 2002

(65) Prior Publication Data

US 2003/0105072 A1 Jun. 5, 2003

Related U.S. Application Data

(60) Provisional application No. 60/287,138, filed on Apr. 27, 2001.

(51) Int. Cl.
*A05N 25/00* (2006.01)
*C07D 205/02* (2006.01)

(52) U.S. Cl. ........................ 424/405; 540/362
(58) Field of Classification Search ................ 540/362; 548/953; 424/405
See application file for complete search history.

(56) References Cited

U.S. PATENT DOCUMENTS

| | | | |
|---|---|---|---|
| 3,852,283 A | 12/1974 | Dolfini et al. | |
| 4,278,681 A | 7/1981 | Haskell et al. | |
| 4,278,789 A | 7/1981 | Birkenmeyer | |
| 4,782,147 A | 11/1988 | Ochiai et al. | |
| 4,963,548 A | 10/1990 | Lunkenheimer et al. | |
| 5,620,953 A | 4/1997 | Cannova et al. | |
| 5,686,486 A | 11/1997 | Tomich et al. | |
| 5,936,065 A | 8/1999 | Arrhenius et al. | |
| 6,143,776 A | 11/2000 | Erlanson | |
| 6,288,091 B1 | 9/2001 | Crute et al. | |
| 6,326,190 B1 | 12/2001 | Ceri et al. | |
| 2001/0049975 A1 | 12/2001 | Ceri et al. | |

FOREIGN PATENT DOCUMENTS

| EP | 0208279 A1 | 1/1987 |
|---|---|---|
| EP | 0 220 939 A1 | 5/1987 |
| EP | 0 294 667 B1 | 12/1988 |
| EP | 0 346 847 B1 | 12/1989 |
| EP | 0 541 497 A1 | 5/1993 |
| EP | 0 587 311 A1 | 3/1994 |
| EP | 1 038 972 A2 | 9/2000 |
| EP | 1 160 236 A2 | 12/2001 |
| JP | 52021322 A | 2/1977 |
| JP | 08081488 A | 3/1996 |
| WO | WO 8806885 A1 | 9/1988 |
| WO | WO 9303055 A1 | 2/1993 |
| WO | WO 9640752 A1 | 12/1996 |
| WO | WO 9717958 A1 | 5/1997 |
| WO | WO 9717963 A1 | 5/1997 |
| WO | WO 97/33972 A1 | 9/1997 |
| WO | WO 98/07883 A1 | 2/1998 |
| WO | WO 9857618 A1 | 12/1998 |
| WO | WO 9857932 A1 | 12/1998 |
| WO | WO 9858075 A2 | 12/1998 |
| WO | WO 9905227 A1 | 2/1999 |
| WO | WO 9927786 A1 | 6/1999 |
| WO | WO 9932428 A2 | 7/1999 |
| WO | WO 9939704 A1 | 8/1999 |
| WO | WO 99/43658 A1 | 9/1999 |
| WO | WO 9955368 A1 | 11/1999 |
| WO | WO 0006177 A1 | 2/2000 |
| WO | WO 0028043 A2 | 5/2000 |
| WO | WO 0032152 A2 | 6/2000 |
| WO | WO 0132655 A2 | 3/2001 |
| WO | WO 0144178 A1 | 6/2001 |
| WO | WO 0144179 A1 | 6/2001 |
| WO | WO 0214270 A1 | 2/2002 |

OTHER PUBLICATIONS

Ferreiro et al. "Assignment of the absolute . . . " CA 133:4396 (2000).*
Huang et al. "Absolute configurational . . . " CA 137:294571 (2002).*
Jain et al. "Alpha substituted hydroxamic acid . . . " CA 140:128630 (2003).*
McFeters et al. "Physiological methods to study biofilm disinfection" CA 124:25250 (1995).*
Flemming et al. "Measures against biofoulihg" CA 126:300403 (1997).*
Jass et al. "Biofilms and biofouling" CA 136:244074 (2002).*
Chicurel M. "Slimebusters" Nature vol. 408 (16) p. 284-286 (2000).*

(Continued)

*Primary Examiner*—Celia Chang
(74) *Attorney, Agent, or Firm*—Leonard W. Lewis; Larry L. Huston; David K. Mattheis

(57) ABSTRACT

The present invention provides nitrogen heterocyclic compounds, compositions, and methods for controlling biofilms, i.e., disrupting biofilms, preventing biofilm formation, enhancing biofilms, or modifying biofilms. Methods for screening test compounds for control of biofilms and devices for use therein are also provided.

4 Claims, 4 Drawing Sheets

OTHER PUBLICATIONS

Alcón, et al., "Rh and Ir complexes containing multidentate, $C_2$-symmetry ligands. Structural and catalytic properties in asymmetric hydrogenation", Journal of Organometallic Chemistry, vol. 601, pp. 284-292, (2000), Elsevier Science S.A.

Alcón, et al., "Synthesis of Rh(I) and Ir(I) complexes with chiral $C_2$-multitopic ligands. Structural and catalytic properties", Journal of Organometallic Chemistry, vol. 634, pp. 25-33, (2001), Elsevier Science B.V.

Birkenmeyer, et al., "Synthesis and Antimicrobial Activity of Clindamycin Analogues: Pirlimycin,[1,2] a Potent Antibacterial Agent", J. Med. Chem., vol. 27, pp. 216-223, (1984), American Chemical Society.

Brugger, M., "128. Synthesis von lipophil substituierten ACTH-Peptiden", Helvetica Chimca Acta, vol. 54, pp. 1261-1274, (1971), Verlag Helvetica Chimca Acta. (English Abstract).

Bulacinski, et al., "Synthesis of acyclic and heterocyclic derivatives of 2-carboxyquinuclidine", Acta Pol. Pharm., vol. 41, No. 3, pp. 313-317, (1984), American Chemical Society. (Abstract).

Bulacinski, et al., "Synthesis of acyclic and heterocyclic derivatives of 2-carboxyquinuclidine. II", Acta Pol. Pharm., vol. 41, No. 4, pp. 441-446, (1984), American Chemical Society. (Abstract).

Charlet-Fagnère, et al., "Syntheses of Large-Ring Bis-Indolic Dilactams", Tetrahedron Letters, vol. 40, pp. 1685-1688, (1999), Elsevier Science Ltd.

Chen, et al., "Synthesis of new substance P analogues releasing histamine from rat peritoneal mast cells", Eur. J. Med. Chem., vol. 27, pp. 931-937, (1992), Elsevier.

Colleti, et al., "Broad Spectrum Antiprotozoal Agents that Inhibit Histone Deacetylase: Structure-Activity Relationships of Apicidin. Part 2", Bioorganic & Medicinal Chemistry Letters, vol. 11, pp. 113-117, (2001), Elsevier Science Ltd.

Emmer, et al., "Derivatives of a Novel Cyclopeptolide. 1. Synthesis, Antifungal Activity, and Structure-Activity Relationships", J. Med. Chem., vol. 37, pp. 1908-1917, (1994), American Chemical Society.

Estrada, et al., "In Silico Studies for the Rational Discovery of Anticonvulsant Compounds", Bioorganic & Medicinal Chemistry Letters, vol. 8, pp. 2755-2770, (2000), Elsevier Science Ltd.

Ferreiro, et al., "Assignment of the Absolute Configuration of a α-Chiral Carboxylic Acids by $^1$H NMR Spectroscopy", J. Org. Chem., vol. 65, pp. 2658-2666, (2000), American Chemical Society.

Fujita, et al., "7-(2-Aminomethyl-1-azetidinyl)-4-oxoquinoline-3carboxylic Acids as Potent Antibacterial Agents: Design, Synthesis, and Antibacterial Activity", Chem. Pharm. Bull., vol. vol. 46, No. 5, pp. 787-796, (1998), Pharmaceutical Society of Japan.

Haskell, et al., "Semisynthetic Penicillins. A Structure-Activity Study of a New Series of Acyl Amino Acid—Pyridone and Pyrimidone Amoxicillin Analogs", The Journal of Antibiotics, pp. 862-868, (1981), Japan Antibiotics Research Association.

Haurou, et al., "Enantiomeric resolution of amino acid derivatives by high-performance liquid chromatography an chiral stationary phases derived from L-proline", Journal of Chromatography, vol. 547, pp. 31-44, (1991), Elsevier Science Publishers B.V.

Hill, et al., "Photochemistry of Dipeptides in Aqueous Solution", J. Am. Chem. Soc., vol. 113, pp. 1805-1817, (1991), American Chemical Society.

Hinko, et al., "Anticonvulsant activity of novel derivatives of 2- and 3-piperidinecarboxylic acid in mice and rats", Neuropharmacology, vol. 35, No. 12, pp. 1721-1735, (1997), American Chemical Society. (Abstract).

Ho, et al., "Synthesis of 2-piperidinecarboxylic acid derivatives as potential anticonvulsants", Eur. J. Med. Chem., vol. 33, pp. 23-31, (1998), Elsevier, Paris.

Hopkins, et al., "Synthesis and Structure of Chiral Macrocycles Containing 2,2'-Bipyridine Subunits", Bioorganic & Medical Chemistry, vol. 4, No. 7, pp. 1121-1128, (1996), Elsevier Science Ltd.

Johnson, et al., "Dopamine Receptor Modulation by Pro—Leu—Gly—$NH_2$ Analogues Possessing Cyclic Amino Acid Residues at the C-Terminal Position", J. Med. Chem., vol. 29, pp. 2100-2104, (1986), American Chemical Society.

Johnson, et al., "Synthesis of Pro—Leu—Gly—$NH_2$ Analogues Modified at the Prolyl Residue and Evaluation of Their Effects on the Receptor Binding Activity of the Central Dopamine Receptor Agonist, ADTN", J. Med. Chem., vol. 29, pp. 2104-2107, (1986), American Chemical Society.

Jun, et al., "Stereochemistry of Complexes of Multidentate Ligands. III. Stereoselective Cobalt(III) Ion Complexes of 1,6-Bis(2(S)-pyrrolidyl)-2,5-diazahexane", Inorganic Chemistry, vol. 14, No. 10, pp. 2310-2314, (1975), American Chemical Society.

Jun, et al., "Stereochemistry of Complexes of Multidenate Ligands. V. Steroselective Cobalt(III) Ion Complexes of N, N'-Bis(2-S-Pyrrolidymethyl)-trans-R-1,2-Cyclohexanediamine", Inorganic Chimica Acta, vol. 15, pp. 111-116, (1975), Elsevier Sequoia S.A., Lausanne.

Kitagawa, et al., "New Nickel(II) Complexes of Some Optically Active Tetraamines with Pyrrolidinyl Groups", Inorganic Chemistry, vol. 14, No. 10, pp. 2347-2352, (1975), American Chemical Society.

Kuwano, et al., "Preparation of some antimicrobial glutamic acid derivatives", J. Fac. Agric., Kyushu Univ., vol. 19, pp. 83-90, (1975), American Chemical Society. (Abstract).

Kuwano, et al., "Catalytic asymmetric hydrogenation of 1-aza-2-cycloalkene-2-carboxylates catalyzed by a trans-chelating chiral diphosphine PhTRAP-rhodium complex", Tetrahedron Letters, vol. 40, pp. 9045-9049, (1999), Elsevier Science Ltd.

Lannoye, et al., "N-Fluoralkylated and N-Alkylated Analogues of the Dopaminergic D-2 Receptor Antagonist Raclopride", J. Med. Chem., vol. 33, pp. 2430-2437, (1990), American Chemical Society.

Lebedeva, et al., "The synthesis and antiviral activity of some aliphatic amides of N-substituted prolines", Khim-Farm. Zh., vol. 2, No. 4, pp. 22-25, (1968), American Chemical Society. (Abstract).

Lee, et al., "Development of a New Type of Protease Inhibitors, Efficacious against FIV and HIV Variants", J. Am. Chem. Soc., vol. 121, pp. 1145-1155, (1999), American Chemical Society.

Lehr, M., "Structure-activity relationships studies on (4-acylpyrrol-2-yl)alkanoic acids as inhibitors of the cytosolic phospholipase $A_2$: Variation of the alkanoic acid substituent, the acyl chain and the position of the pyrrole nitrogen", Eur. J. Med. Chem., vol. 32, pp. 805-814, (1997), Elsevier, Paris.

Lehr, M., "Synthesis, Biological Evaluation, and Structure-Activity Relationships of 3-Acylindole-2-carboxylic Acids as Inhibitors of the Cytosolic Phospholipase $A_2$", J. Med.

Chem., vol. 40, pp. 2694-2705, (1997), American Chemical Society.

Lentini, et al., "Peptides with Alkyl groups at the N- or C-Terminus", Biol. Chem. Hoope-Seyler, vol. 368, pp. 369-378, (1987), Walter de Gruyter & Co. (English Abstract).

Likhosherstov, et al., "Azacycloalkanes. XX. Derivatives of hexahydroazepine-2-carboxylic acid", Khim.-Farm. Zh., vol. 12, No. 4, pp. 58-62, (1978), American Chemical Society. (Abstract).

Lim, et al., "Asymmetric Syntheses of Fused Bicyclic Lactams", J. Org. Chem., vol. 66, pp. 9056-9062, (2001), American Chemical Society.

Marastoni, et al., "HIV-1 Protease Inhibitors Containing an N-Hydroxyamino Acid Core Structure", Bioorganic & Medicinal Chemistry, vol. 9, pp. 939-945, (2001), Elsevier Science Ltd.

Martin, et al., "Syntheses of R and S Isomers of AF-DX384, a Selective Antagonist of Muscarinic $M_2$ Receptors", Bioorganic & Medicinal Chemistry Letters, vol. 8, pp. 591-600, (2000), Elsevier Science Ltd.

Mauger, et al., "Synthesis and Properties of Some Peptide Analogues of Actinomycin D", J. Med. Chem., vol. 34, pp. 1297-1301, (1991), American Chemical Society.

Mimoto, et al., "Structure-Activity Relationship of Orally Potent Tripeptide-Based HIV Protease Inhibitors Containing Hydroxymethylcarbonyl Isostere", Chem. Pharm. Bull., vol. 48, No. 9, pp. 1310-1326, (2000), Pharmaceutical Society of Japan.

Murray, et al., "the Synthesis of Cyclic Tetrapeptoid Analogues of the Antiprotozoal Natural Product Apicidin", Bioorganic & Medicinal Chemistry Letters, vol. 11, pp. 773-776, (2001), Elsevier Science Ltd.

Nakajima, et al., "The reaction of ω-hydroxy-α-amino acid derivatives with Mitsunobu reagents", Pept. Chem., vol. 21, pp. 77-80, (1984), American Chemical Society. (Abstract).

Okawa, et al., "Total synthesis of actinomycin D." Pept. Chem., vol. 15, pp. 131-134, (1977), American Chemical Society. (Abstract).

Overberger, et al., "Synthesis and Optical Properties of Polyethylenimine Containing L-Proline and Optically Active Thymine Derivatives", Journal of Polymer Science: Polymer Chemistry Edition, vol. 18, pp. 1433-1446, (1980), John Wiley & Sons, Inc.

Pettit, et al., "Antimicrobial and cancer cell growth inhibitory activities of 3β-acetoxy-17β-(L-prolyl)amino-5α-androstane in vitro", International Journal of Antimicrobial Agents, vol. 15, pp. 299-304, (2000), Elsevier Science B.V. and International Society of Chemotherapy.

Phillips, et al., "Azetidine-2-carboxylic Acid Derivatives", Department of Chemistry, University of Nebraska, vol. 10, pp. 795-799, (1973), publisher unknown.

Reich, et al., "Structure-Based Design and Synthesis of Substituted 2-Butanols as Nonpeptidic Inhibitors of HIV Protease: Secondary Amide Series", J. Med. Chem., vol. 39, pp. 2781-2794, (1996), American Chemical Society.

Rinehart, et al., "Structures of the Didemnins, Antiviral and Cytotoxic Depsipeptides from a Caribbean Tunicate", J. Am. Chem. Soc., vol. 103, pp. 1857-1859, (1981), American Chemical Society.

Rodebaugh, et al., "2-Carboazetidine Derivatives (1)", Department of Chemistry, University of Nebraska, vol. 8, pp. 19-24, (1971), Dissertation Abstracts International, Oct. 1970.

Schlunsen, et al., "Spezifishe Adsorbentien für das Peptidantibiotika synthetisierende Enzymsystem Gramicidin S Synthetase, 1", Makromol. Chem., vol. 188, pp. 3005-3016, (1987), publisher unknown. (English Abstract).

Schutkowski, et al., "Synthesis of dipeptide 4-nitroanilides containing non-proteinogenic amino acids", Int. J. Pept, Protein Res., vol. 45, No. 3, pp. 257-265, (1995), American Chemical Society. (Abstract).

Sendai, et al., "Synthesis of Carumonam (AMA-1080) and a Related Compound Starting from (2R,3R)-Epoxysuccinic Acid", Chem. Pharm. Bull., vol. 33, No. 9, pp. 3798-3810, (1985), Pharmaceutical Society of Japan.

Sikorski, et al., "Selective Peptidic and Peptidomimetic Inhibitors of Candida albicans MyristoylCoA: Protein N-Myristoyltransferase: A New Approach to Antifungal Therapy", Biopolymers, vol. 43, No. 1, pp. 43-71, (1997), John Wiley & Sons, Inc.

Singh, et al., "Structure and Chemistry of Apicidins, a Class of Novel Cyclic Tetrapeptides without a Terminal α-Keto Epoxide as Inhibitors of Histone Deacetylase with Potent Antiprotozoal Activities", J. Org. Chem., vol. 67, pp. 815-825, (2002), American Chemical Society.

Sole, et al., "Mixed Anhydrides in Peptide Synthesis. Factors Affecting Urethane Formation and Racemization", Tetrahedron, vol. 42, No. 1, pp. 193-198, (1986), Pergamon Press Ltd.

Sole, et al., "Synthesis of hydrophobic enkephalin amides", Int. J. Peptide Protein Res., vol. 26, pp. 591-597, (1985), Munksgaard International Publishers Ltd.

Starmans, et al., "Enzymatic resolution of methyl N-alkyl-azetidine-2-carboxylates by Candida antarctica lipase-mediated ammoniolysis", Tetrahedron: Asymmetry, vol. 9, pp. 429-435, (1998), Elsevier Science Ltd.

Takeuchi, et al., "Asymmetric hydrogenation catalyzed by the (achiral base)bis(dimethylglyoximato)cobalt(II)-chiral cocatalyst system. The preparation of a new type of chiral cocatalyst and its application to the asymmetric hydrogenation of methyl α-acetamidoacrylate)acrylate and benzil.", Bull. Chem. Soc. Jpn., vol. 54, No. 7, pp. 2136-2141, (1981), American Chemical Society. (Abstract).

Tapuhi, et al., "Practical Considerations in the Chiral Separation of Dns-Amino Acids by Reversed-Phase Liquid Chromatography Using Metal Chelate Additives", Journal of Chromatography, vol. 205, pp. 325-337, (1981), Elsevier Scientific Publishing Company.

Uchiyama, et al., "Synthesis of hybrid type of anti-HIV drugs", Pept. Chem., vol. 31, pp. 89-92, (1993), American Chemical Society. (Abstract).

Vecchietti, et al., "(2S)-1-(Arylacetyl)-2(aminomethyl) piperidine Derivatives: Novel, Highly Selective κ Opioid Analgesics", J. Med. Chem., vol. 34, pp. 397-403, (1991), American Chemical Society.

Wang, et al., "Synthesis and Evaluation of Tryprostatin B and Demethoxyfumitremorgin C Analogues", J. Med. Chem., vol. 43, pp. 1577-1585, (2000), American Chemical Society.

* cited by examiner

US 7,018,642 B2

COMPOUNDS, COMPOSITIONS, AND METHODS FOR CONTROLLING BIOFILMS

CROSS REFERENCE TO RELATED APPLICATIONS

The present application claims the benefit of U.S. Ser. No. 60/287,138, filed Apr. 27, 2001.

FIELD OF INVENTION

This invention relates to compounds, compositions, and methods for controlling biofilms, i.e., disrupting biofilms, preventing biofilm formation, enhancing biofilms, or modifying biofilms. Methods for screening test compounds for control of biofilms and devices for use therein are also provided.

BACKGROUND OF THE INVENTION

Biofilms are mucilaginous communities of microorganisms such as bacteria, archaea, fungi, molds, algae or protozoa or mixtures thereof that grow on various surfaces (see *Nature*, vol. 408, pp. 284–286, Nov. 16, 2000). Biofilms form when microorganisms establish themselves on a surface and activate genes involved in producing a matrix that includes polysaccharides. This matrix may provide protection of biofilm bacteria from biocides.

Molecules called quorum-sensing signals help trigger and coordinate part of the process of forming a biofilm. Bacteria constantly secrete low levels of the signals and sense them either through receptors on their surfaces, or internally. The receptors trigger behavioral changes when there are enough bacteria to allow the signals' concentrations to achieve a critical threshold. Once this occurs, bacteria respond by adopting communal behavior, such as forming a biofilm, and in the case of pathogenic bacteria, deploying virulence factors such as toxins. In addition to communicating with members of their own species, bacteria also conduct inter-species communications, such that a biofilm may contain more than one species of bacteria.

Biofilms are frequently undesirable. For example, biofilms cause damage by coating equipment such as cooling systems, or aquaculture equipment. Biofilms can also have detrimental health effects. For example, many hospital-acquired infections involve biofilms, which can contaminate implants and catheters. Dental lines are prime candidates for biofilm formation. Biofilms also cause diseases ranging from lung infections in cystic fibrosis patients to tooth decay.

However, biofilms can also be desirable. For example, biofilms are used in bioreactors used for such tasks as manufacturing pharmaceuticals, and biofilms are also components in sewage and other water treatment systems.

One method for preventing or disrupting a biofilm is to interfere with the quorum-sensing signals. Chemicals have been developed that bind but fail to activate the receptors of quorum-sensing signals or that interfere with signal synthesis. Enzymes that degrade the signals have also been developed. Certain quorum-sensing signals typically have acylated homoserine lactone ring systems. WO 00/06177 reportedly provides methods for identifying modulators of the autoinducer synthesis reaction that promote or inhibit production of homoserine lactone. WO 00/32152 reportedly provides a bacterial signaling factor 4,5-dihydroxy-2,3-pentanedione, wherein the factor assists in inducing expression of luminescence genes.

There is an ongoing need to identify agents that modulate biofilm formation and growth, as well as methods and devices for testing such formation and growth. The present invention addresses these problems and provides certain nitrogen heterocyclic molecules that modulate such processes, as well as methods and devices for testing such modulation.

SUMMARY OF THE INVENTION

This invention relates to compounds, compositions, and methods for controlling biofilms. "Controlling" a biofilm means disrupting a biofilm and/or preventing biofilm formation, enhancing formation and/or growth of a biofilm, or modifying a biofilm. This invention further relates to assays and methods for determining the effect of a compound on a biofilm. Apparatuses for testing biofilm control on a substrate surface are also provided.

All documents cited are, in relevant part, incorporated herein by reference; the citation of any document is not to be construed as an admission that it is prior art with response to the present invention.

DETAILED DESCRIPTION OF THE INVENTION

Figure 1:
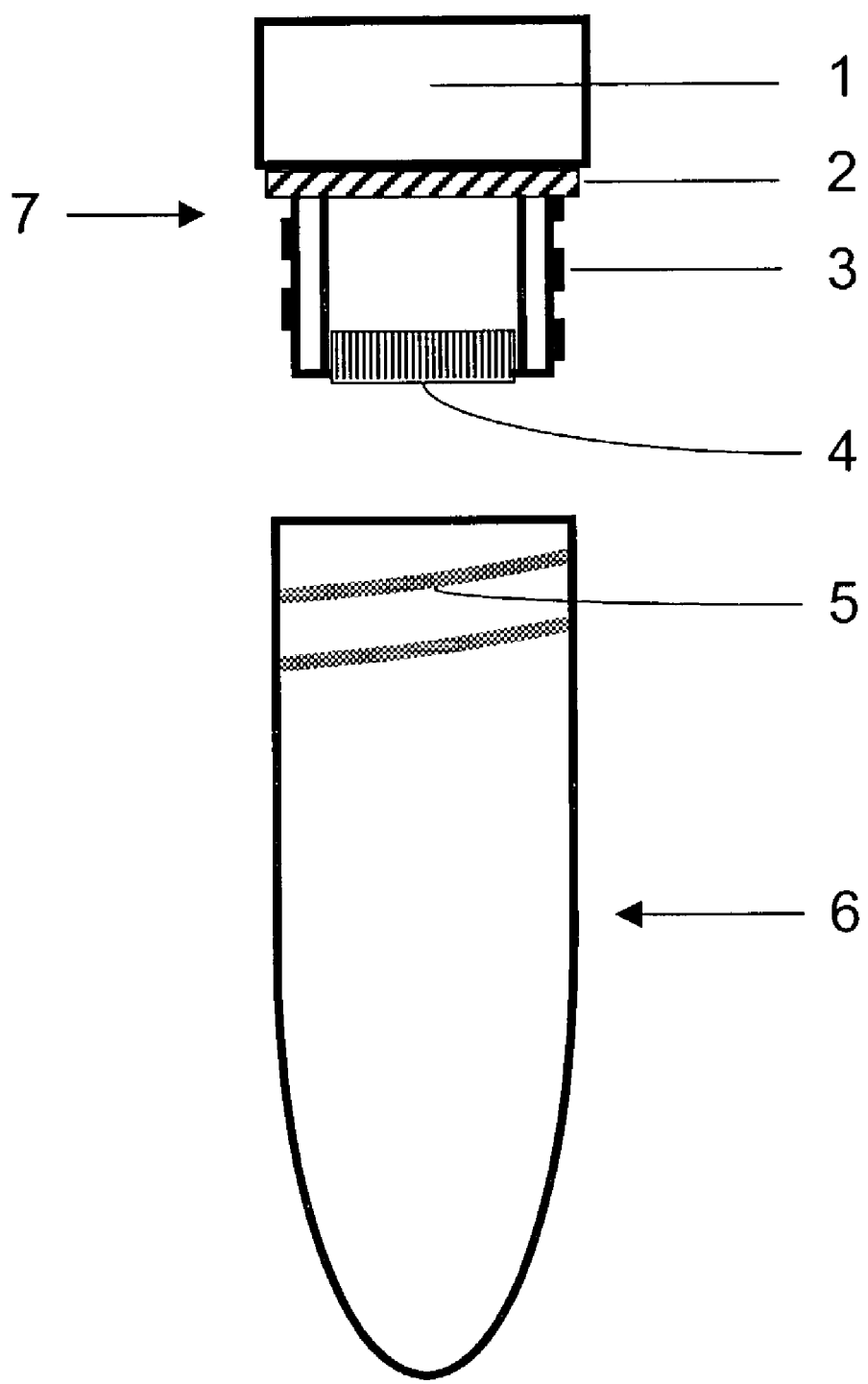
FIG. 1 is a side cross sectional view of the plastic tube-based biofilm growth and test method invention described in Assay Reference Example 4.

The present invention provides compounds and methods for controlling biofilms on a substrate surface. The invention also provides methods for screening test compounds for activity in controlling biofilms, and apparatuses for testing biofilm control on substrate surfaces. "Biofilm" means a mucilaginous community of microorganisms, such as, for example, bacteria, archaea, fungi, molds, algae or protozoa that can grow on various substrates. A biofilm can comprise one or more than one species. "Substrate" means any surface on which a biofilm can form or has formed. Substrate includes, but is not limited to, hard or soft surfaces such as polymers, plastics, tubing, ceramics, metals, glass, hydroxyapatite, skin, bone, or tissues.

"Controlling biofilms" means herein to disrupt a biofilm and/or prevent biofilm formation, to enhance formation and/or growth of a biofilm, or to modify a biofilm. The invention provides nitrogen heterocyclic compounds having structure A or structure B for controlling biofilms, or a combination thereof, a salt thereof, or a stereoisomer thereof. A method of controlling biofilm on a substrate comprises contacting the substrate with a compound having structure A or having structure B as set forth herein for a time sufficient to control the biofilm on the substrate.

Structure A:

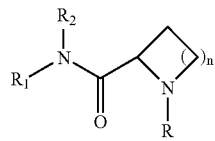

For compounds used for controlling biofilms having structure A, n is 1–4, and R is H, alkyl, acyl, or alkoxycarbonyl. Further, when n is 1, $R_1$ and $R_2$ are independently H, $C_6$–$C_{20}$ alkyl, or alkenyl; wherein when R is H, one of $R_1$ and $R_2$ is other than H. When n is 2, $R_1$ and $R_2$ are independently H; $C_4$–$C_{20}$ alkyl, or alkenyl; wherein when R is H, one of $R_1$ and $R_2$ is other than H. When n is 3, $R_1$ and $R_2$ are independently H; $C_5$–$C_{20}$ alkyl, or alkenyl; wherein when R is H, one of $R_1$ and $R_2$ is other than H. When n is 4, $R_1$ and $R_2$ are independently H; $C_1$–$C_{20}$ alkyl, or $C_2$–$C_{20}$ alkenyl.

Structure B:

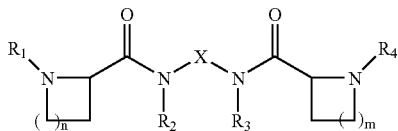

For compounds used for controlling biofilms having structure B, n and m are independently 1, 2, 3, or 4; X is $C_1$–$C_{20}$ alkyl, or $C_2$–$C_{20}$ alkenyl; $R_1$ and $R_4$ are independently H, alkyl, acyl or alkoxycarbonyl, and $R_2$ and $R_3$ are independently H, or alkyl; with the proviso that when n and m are 2, X is $C_8$–$C_{20}$ alkyl or $C_8$–$C_{20}$ alkenyl. Salts, stereoisomers, or combinations of the nitrogen heterocyclic compounds provided herein are contemplated by the present inventors as useful for controlling biofilms.

New compounds having structure A or B as set forth infra, or a salt or a stereoisomer thereof, or compositions thereof, are also provided by the present invention. An embodiment of the invention provides compounds having structure A when n is 1, R is H, alkyl, acyl, or alkoxycarbonyl; and $R_1$ and $R_2$ are independently H, $C_6$–$C_{20}$ alkyl, or alkenyl; and wherein when R is H, one of $R_1$ and $R_2$ is other than H. Such compounds are synthesized as shown, for example, in synthesis examples 1–3 herein. One of skill in the art in light of the examples herein would be able to synthesize compounds having related substituents. Compounds in which $R_1$ and $R_2$ are independently alkenyl are prepared as in example 2 using the appropriate alkenyl amine in place of n-decylamine. Compounds in which R is alkyl are prepared as in example 2 from the appropriate 1-alkyl-2-azetidinecarboxylic acid, the synthesis of which is described by Cromwell et al. in *J. Heterocyclic Chem.* (1968), 5(2), 309–311. Compounds in which R is acyl are prepared by reacting the appropriate 2-azetidinecarboxylic acid amide with an acid chloride in a manner similar to example 9.

A further embodiment of the invention provides new compounds having structure A when n is 3, R is H, alkyl, acyl, or alkoxycarbonyl; and $R_1$ and $R_2$ are independently H; $C_5$–$C_{20}$ alkyl, or alkenyl; and wherein when R is H, one of $R_1$ and $R_2$ is other than H. Such compounds are synthesized as shown, for example, in synthesis examples 7–9 herein. One of skill in the art in light of the examples herein would be able to synthesize compounds having related substituents. Compounds in which $R_1$ and $R_2$ are independently alkenyl are prepared as in example 7 using the appropriate alkenyl amine in place of n-octylamine. Compounds in which R is alkyl are prepared as in example 7 from the appropriate 1-alkyl-2-piperidinecarboxylic acid, which is available through the reductive alkylation of 2-piperidinecarboylic acid as described by Hu et al. in WO 9943658.

A further embodiment of the invention provides new compounds having structure A when n is 4, R is H, alkyl, acyl, or alkoxycarbonyl; and $R_1$ and $R_2$ are independently H; $C_5$–$C_{20}$ alkyl, or alkenyl. Such compounds are synthesized as shown, for example, in synthesis examples 10 and 11 herein. One of skill in the art in light of the examples herein would be able to synthesize compounds having related substituents. Compounds in which R is acyl are prepared by reacting the appropriate 2-azepanecarboxylic acid amide with an acid chloride in a manner similar to example 9. Compounds in which R is alkyl are prepared as in example 10 from the appropriate 1-alkyl-2-azepanecarboxylic acid, which is available through the reductive alkylation of 2-azepanecarboxylic acid. The synthesis of 2-azepanecarboxylic acid has been described by Seebach et al. (*Liebigs Ann. Chem.* (1989), (12), 1215–1232). Compounds in which $R_1$ and $R_2$ are H are prepared by the method in example 10 using ammonia in place of n-octylamine or by the method described by Cromwell et al. in *J. Heterocyclic Chem.* (1971), 8(1), 19–24.

A further embodiment of the invention provides new compounds having structure B where n and m are independently 1, 2, 3, or 4; X is $C_1$–$C_{20}$ alkyl, or $C_2$–$C_{20}$ alkenyl; $R_1$ and $R_4$ are independently H, alkyl, acyl or alkoxycarbonyl, and $R_2$ and $R_3$ are independently H, or alkyl; with the proviso that when n and m are 2, X is $C_8$–$C_{20}$ alkyl or alkenyl. Such compounds are synthesized as shown, for example, in synthesis examples 12 and 13 herein. One of skill in the art would also know in light of the present disclosure how to make compounds where n and m are independently 1, 2, 3, or 4 in light of examples 1–13.

"Alkyl" refers to a fully saturated monovalent hydrocarbon radical of 1 to 20 carbon atoms unless otherwise specified. The alkyl may be straight-chain or branched. Preferred are those alkyl groups containing 4, 5, or 6 to 20 carbon atoms, with 4, 6, 8, 10, or 12 carbon atoms particularly preferred. "Acyl" refers to a group having a carbonyl. "Alkoxycarbonyl" refers to —COOR where R is alkyl. "Alkenyl" refers to an unsaturated monovalent hydrocarbon radical of 2 to 20 carbon atoms having one or more double bonds. The alkenyl may be straight-chain or branched. Preferred are those alkenyl groups containing 4 to 20 carbon atoms, with 8, 10, or 12 carbon atoms particularly preferred.

"Independently" means that two or more of the groups immediately preceding the term are either identical or different; i.e., selection of one from the list following the term does not affect selection of the other(s).

A "salt thereof" is a salt of a nitrogen heterocyclic compound as provided herein with an organic or inorganic acid, such as, for example, chloride, bromide, sulfate, nitrate, phosphate, sulfonate, formate, tartrate, maleate, malate, citrate, benzoate, salicylate, ascorbate, or others known to those of ordinary skill in the art in light of the present disclosure.

Control of biofilm by a nitrogen heterocyclic compound as provided herein is determined by assaying the amount of biofilm resulting from treatment in the presence of a test compound as compared to the amount resulting from treatment in the absence of a test compound. A change in the amount of biofilm present as a result of a treatment may result from an effect on the exopolysaccharide matrix of biofilm or an effect on a microorganism within the biofilm, or an effect on the relationship therebetween. Not wanting to be bound by theory, the present inventors believe the nitrogen heterocyclic molecules of the present invention may be mimicking, interfering with or modifying an action of quorum sensing molecules in biofilm communication. The present compounds may also modify a biofilm by, for example, decreasing toxin production, decreasing virulence, by interfering with signal molecules, or by increasing levels of an enzyme that is produced by the biofilm, for example, in a bioreactor.

A "test compound" is a candidate compound for screening for activity in controlling biofilms. The examples herein test biofilm dispersion and formation in bacterial species that are relevant to consumer and medical environments, and that are broadly representative of bacterial cell wall type. *Pseudomonas* species are tested since these are widespread in biofilms that form in high humidity environments, such as those present in and around showers, toilets, sinks, and drains, and since these are representative gram negative bacteria. *Staphylococcus epidermidis* is tested since it is commonly found on human skin and since it is a representative gram positive bacterium. Both *P. aeruginosa* and *S. epidermidis* are medically important, being opportunistic pathogens and frequent causative agents in hospital-acquired infections, where growth of these organisms in a biofilm state is thought to be important. In addition, these three organisms represent a range of difficulty in treating biofilms, *P. aeruginosa* being the most difficult to control. Screening approaches described herein are also applicable to other bacteria and fungi, including *Staphylococcus aureus, Candida albicans*, or *Malassezia furfur*, for example.

Measurement of biofilm growth herein uses crystal violet as a quantitative, total biofilm staining dye that stains both cells and extracellular polysaccharide, to rapidly identify compounds that are active in controlling biofilms of *P. aeruginosa, P. fluorescens*, and *S. epidermidis*. Further dyes or assays also may be used for quantification of biofilms in a similar manner, including but not limited to polysaccharide stains, DNA stains, chemical or biochemical assays, enzyme assays, or physical methods. Such methods are generally destructive to the cells contained within the biofilm.

Non-destructive alternative methods may also be used for quantification of extent of compound activity in controlling biofilms. Cells may be released intact from biofilms by physical, chemical, or biological methods such as scraping, sonication, agitation in buffer ('stomaching'), shaking with glass beads, chemicals, enzymes, or other methods known to those skilled in the art in the light of the present disclosure. Released cell numbers are then measured using methods such as classical bacteriological viable cell counting using agar plates, using fluorescent or non-fluorescent viable or total cell stains with or without fluorescence activated cell sorting, light scattering techniques, image analysis, enzyme assays, or biochemical methods. Other methods known to those skilled in the art in the light of the present disclosure may also be used, however it is contemplated that the easiest and most cost-effective method currently available is the crystal violet method described herein.

Assay methods disclosed herein are "functional" in the sense that they measure the degree of biofilm control by compounds, irrespective of mechanism. Hence, the assays do not discriminate between compounds that are cidal, static, or non-inhibitory to bacterial growth, in spite of their activity in controlling biofilms. Additional assays would shed light on mechanism of activity of such active compounds, such as minimum inhibitory concentration assays, growth rate assays, non-specific cell lysis assays, specific reporter gene or protein based assays, and other assays known to those skilled in the art in light of the present disclosure.

An advantage of the functional assay methods employed in the inventions disclosed herein is that compounds having any of a variety of mechanisms of biofilm control can be discovered using the assays, including compounds acting through presently unknown mechanisms.

Assay methods disclosed herein are particularly suited to the study of biofilms that may be formed on hard surfaces, and their susceptibility to, for example, various cleaning compositions. Small changes that allow adaptations of the methods to other types of surfaces such as soft, porous, or irregular surfaces will be obvious to those skilled in the art in light of the present disclosure.

The present invention also provides a method for amplifying an effect of a compound having biofilm dispersion activity on amount of dispersed biofilm. The method comprises incubating a biofilm with a compound having biofilm dispersion activity for a time sufficient to allow the compound to act to disperse biofilm, adding a base to the biofilm, incubating for a time sufficient to amplify the effect of the compound, and determining the amount of biofilm present. The effect of the compound is amplified in the presence of the base as compared to the effect in the absence of a base. A base may be any base such as NaOH, KOH, or $NH_4OH$, for example. Use of the base in this dispersion assay boosts the sensitivity of the assay as compared to an assay lacking the step of adding a base.

In an embodiment of the method of controlling biofilm on a substrate, the compound has structure A and n is 1; where controlling is enhancement of biofilm formation or enhancement of existing biofilm, R is alkoxycarbonyl, $R_1$ is H, and $R_2$ is $C_{10}$–$C_{12}$ alkyl; and where controlling is prevention of biofilm formation or dispersion of existing biofilm, R and $R_1$ are H, and $R_2$ is $C_6$–$C_{12}$ alkyl.

In another embodiment of the method of controlling biofilm on a substrate, the compound has structure A and n is 2; where controlling is enhancement of biofilm formation or enhancement of existing biofilm, R is alkoxycarbonyl or acyl, $R_1$ is H, and $R_2$ is $C_6$–$C_{12}$ alkyl; and where controlling is prevention of biofilm formation or dispersion of existing biofilm, R and $R_1$ are H, and $R_2$ is $C_{10}$–$C_{12}$ alkyl. In another embodiment, R is H, $R_1$ is H, and $R_2$ is $C_{10}$ alkyl.

In another embodiment of the method of controlling biofilm on a substrate, the compound has structure A and n is 3; alternatively, R is H or alkoxycarbonyl, $R_1$ is H, and $R_2$ is $C_8$ alkyl; and wherein controlling is enhancement of formation of biofilm, R is alkoxycarbonyl, acyl, or H, $R_1$ is H, and $R_2$ is $C_8$ alkyl.

In another embodiment of the method of controlling biofilm on a substrate, the compound has structure A and n is 4.

In another embodiment of the method of controlling biofilm on a substrate, the compound has structure B and n and m are 1, 3 or 4; alternatively, n and m are 2, and preferably, X is $C_{12}$ alkyl, and $R_1$, $R_2$, $R_3$, and $R_4$ are H. Where n and m are 2, and where controlling is enhancement of biofilm formation or enhancement of existing biofilm, X is preferably $C_{12}$ alkyl, $R_2$ and $R_3$ are preferably H, and $R_1$ and $R_4$ are preferably alkoxycarbonyl. Where n and m are 2, and where controlling is prevention of biofilm formation or dispersion of existing biofilm, preferably, X is $C_{12}$ alkyl, and $R_1$–$R_4$ are H.

Applications of Control of Biofilms

The present invention provides methods and compounds for controlling biofilms. The method comprises contacting the substrate with a compound described above. In a preferred embodiment of the invention, the substrate is treated with the compound, e.g., the compound applied to a substrate leaves a residue on the substrate. For control of biofilms, compositions will comprise one or more compounds, for example, at a level of from about 0.001% to about 99%, from about 0.01% to about 50%, or, for example, about 0.1% to about 10% by weight of the composition.

In one embodiment of the invention, a compound and/or composition described above is applied to a substrate in a high humidity environment to disrupt biofilms and/or prevent their formation. The substrate can be a hard surface, including bathroom surfaces such as a shower, toilet or sink, kitchen surfaces such as a sink or waste disposal, or a fabric surface. Alternatively, the compound and/or composition can be used to treat the insides of high-humidity appliances such as dishwashers, refrigerators, etc. Alternatively, the substrate can be another kitchen and/or other surface such as a sponge, cutting board (wood or plastic), or wash cloth. In an alternative embodiment of the invention, the compound and/or composition is used in laundry applications, e.g., applied to the insides of washing machine tubs and/or bowls. The compound or composition may be applied to a fabric. The compound or composition can reduce malodor, assist in cleaning, and/or prevent mold growth on stored fabrics such as clothing, curtains, or the like, in a humid environment.

In an alternative embodiment of the invention, the compound and/or composition can be used to prevent surface fouling with reduced cleaning and/or reduced use of chlorine in pools, spas, and/or hot tubs. In an alternative embodiment of the invention, the compound and/or composition can be used on outdoor substrates such as siding, roofing, decks, and/or patios to prevent outdoor mold and/or algal growth.

In an alternative embodiment of the invention, the compound and/or composition can be used in plant and/or flower care vases and/or aquaria, for example to provide a longer lasting benefit with less cleaning. In an alternative embodiment of the invention, the compound and/or composition can be used in automobile air conditioning units and other air conditioning units prone to biofilm formation to prevent or treat biofilm formation.

In an alternative embodiment of the invention, the compound and/or composition can be used to prevent biofilm formation on home-use water filtration systems (e.g., on filters, housings, and/or delivery lines) and industrial water cooling and/or treatment systems. In an alternative embodiment of the invention, the compound and/or composition can be used to prevent biofilm formation by basement molds.

In an alternative embodiment of the invention, the compound or composition can be used as an antiinfective such as in combination with another antimicrobial, such as an antibiotic. The compound or composition may be used to treat a subject for a disease state associated with biofilm development, such as a bacterial infection, for cystic fibrosis or HIV, or for an immunocompromised subject. Alternatively, the compound and/or composition can be used as a treatment for medical or dental devices such as catheters, tubing, prostheses, etc. to prevent or treat biofilm formation thereon. In an alternative embodiment of the invention, the compound and/or composition can be used in oral care applications such as on teeth or dentures to control plaque and/or odor.

In an alternative embodiment of the invention, the compound and/or composition can be used to control biofilm formation on skin, e.g., for dandruff control (prevention of *Malassezia* biofilms on scalp), in hand/skin sanitizers (prevention of growth or restoration of natural microflora), for deodorant applications, or for foot care (prevention of fungal growth such as Athletes' Foot without disrupting natural microflora). In an alternative embodiment of the invention, the compound and/or composition can be used in shoe care applications to control bacterial and/or fungal biofilm formation on shoe surfaces. In an alternative embodiment of the invention, the compound and/or composition can be used to prevent toxic shock syndrome or to restore imbalanced microflora (e.g., occluded skin in for example, diapers, or the vaginal tract).

In an alternative embodiment of the invention, the compound and/or composition can be used in any process machinery having metal, ceramic, glass, composite, or polymer parts, particularly in paper, food, drug, and cosmetic processing applications. The compound and/or composition can be used to prevent biofilm formation on metal, ceramic, glass, composite, or polymer parts and to prevent growth of fungal or bacterial biofilms in paper products.

In an alternative embodiment of the invention, the compound and/or composition can be used as a food and/or beverage preservative.

In an alternative embodiment of the invention, the compound and/or composition can be used in generalized surface coatings to prevent biofouling (e.g. paints or coatings for houses, boats, fabrics, carpets, shoes, etc.). In an alternative embodiment of the invention, the compound and/or composition can be used in generalized impregnated materials (e.g. plastics, wood, composites) or controlled delivery systems. In an alternative embodiment of the invention, the compounds and/or compositions can be used in construction applications such as materials protection (e.g., wood, siding, roofs, etc.) and equipment protection. In an alternative embodiment of the invention the compounds and/or compositions can be used in marine and freshwater biofouling prevention (e.g., on boats, docks, jettys, buoys, ropes, and military applications).

In an alternative embodiment of the invention, the compounds and/or compositons can be used in bioprocessing applications for promotion of optimal biofilm formation in, for example, wastewater treatment systems/plants, bioremediation systems, or bioprocessing systems (e.g. whole-cell biocatalysis).

In an alternative embodiment of the invention, the compounds and/or compositions can be used in agricultural applications such as crop protection, crop nutrition (promotion of desirable biofilms), and prevention of runoff-mediated fouling (e.g., in ditches, pumps, etc.).

In an alternative embodiment of the invention, the compounds and/or compositions can be used in aquaculture applications such as disease prevention and promotion of optimal skin biofilms.

Pharmaceutical Dosages, Formulations and Administration

For pharmaceutical applications, a "therapeutically effective amount" means the concentration or quantity or level of the compound of the present invention that can attain a particular medical end in controlling biofilms, such as decreasing biofilm formation, dispersing biofilms, or having toxic activity for biofilms. The specific "therapeutically effective amount" will vary with such factors as the particular condition being treated, the physical condition of the patient, the type of mammal being treated, the duration of the treatment, the nature of concurrent therapy (if any), and the specific formulations employed and the structure of the compounds or its salts.

Any suitable dosage may be administered in the pharmaceutical methods of the present invention. The dosage administered will vary depending upon known factors, such as the pharmacodynamic characteristics of the particular compound, salt, or combination and its mode and route of administration; the age, health, or weight of the subject; the nature and extent of symptoms; the metabolic characteristics of the drug and patient, the kind of concurrent treatment; the frequency of treatment; or the effect desired. Effective doses may be extrapolated from dose response curves from animal model test systems or in vitro test systems.

A dosage unit may comprise diluents, extenders, carriers, liposomes, or the like. The unit may be in solid or gel form such as pills, tablets, capsules and the like or in liquid form suitable for oral, rectal, topical, intravenous injection or parenteral administration or injection into or around the treatment site. The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin, cyclodextrin derivatives, or the like. Topical applications for administration according to the method of the present invention include ointments, cream, suspensions, lotions, powder, solutions, pastes, gels, spray, aerosol or oil. Formulations suitable for nasal administration may be administered in a liquid form, for example, nasal spray, nasal drops, or by aerosol administration by nebulizer, including aqueous or oily solutions of the active ingredient. Formulations suitable for parenteral administration include aqueous and non-aqueous formulations isotonic with the blood of the intended recipient; and aqueous and non-aqueous sterile suspensions which may include suspending systems designed to target the compound to blood components or one or more organs.

A prodrug refers to a form of the compounds provided herein that has minimal therapeutic activity until it is converted to its desired biologically active form. A prodrug is a compound having one or more functional groups or carriers covalently bound thereto, which functional groups or carriers are removed from the compound by metaboic processes within the body to form the respective bioactive compound. Prodrugs include compounds wherein hydroxy, or amine groups, for example, are bonded to any group that, when administered to a mammalian subject, cleaves to form a free hydroxyl, or amino group, respectively. Examples of prodrugs include, but are not limited to, acetate, formate, or benzoate derivatives of alcohol and amine functional groups, phosphate esters, dimethylglycine esters, aminoalkylbenzyl esters, aminoalkyl esters or carboxyalkyl esters of functional groups.

A metabolite refers to a break-down or end product of a compound of the present invention or its salt produced by metabolism or biotransformation; e.g., biotransformation to a more polar molecule such as by oxidation, reduction, or hydrolysis, or to a conjugate. The metabolite of a compound or its salt may be a more biologically active form. An assay for activity of a metabolite of a compound of the present invention is known to one of skill in the art in light of the present disclosure, for example, testing for biofilm dispersion or prevention.

Adjunct Ingredients

The present invention further provides compositions comprising one or more of the compounds described above and one or more adjunct ingredients. For example, the composition contains about 0.0001% to about 50% of a compound described above, and the balance adjunct ingredients. Examples of adjunct ingredients include, but are not limited to, antibiotics, biocides, builders, bleaches, bleach activators, bleach catalysts, carrier, divalent cations, enzymes, enzyme stabilizing systems, chelants, optical brighteners, soil release polymers, dye transfer agents, dispersants, suds suppressors, dyes, colorants, filler salts, hydrotropes, photoactivators, fluorescers, fabric conditioners, surfactants including hydrolyzable surfactants, perservatives, anti-oxidants, anti-shrinkage agents, anti-wrinkle agents, other antimicrobial agents, germicides, fungicides, color speckles, silvercare, anti-tarnish and/or anti-corrosion agents, antifoaming agents, alkalinity sources, solvents, solubilizing agents, carriers, processing aids, pigments, perfumes, or pH control agents. The surfactant can be nonionic, anionic, amphoteric, amphiphilic, zwitterionic, cationic, semi-polar nonionic, or mixtures thereof.

Compositions of the present invention may comprise a solvent or mixtures thereof. Suitable solvents for incorporation in the compositions according to the present invention include aqueous-based, or organic-based solvents. A solvent may contain water, saline, buffered saline, dextrose, glycerol, ethanolamine, alcohols, propylene glycol derivatives such as n-butoxypropanol or n-butoxypropoxypropanol, 2-(2-alkoxyethoxy)ethanol, 2-alkoxyethoxyethanol, or poly (alkylene glycol)alkyl ether, in particular, n-butoxypropoxypropanol, butyl CARBITOL®, monoethanolamine (MEA), diethanolamine, triethanolamine, benzyl alcohol, methanol, ethanol, isopropyl alcohol or diols such as 2-ethyl-1,3-hexanediol and 2,2,4-trimethyl-1,3-pentanediol or mixtures thereof. Further, non-vicinal $C_4$–$C_8$ branched or straight chain alkylene glycols, such as hexylene glycol, (4-methyl-2,4-pentanediol), 1,6-hexanediol, 1,3-butylene glycol and 1,4-butylene glycol are solvent embodiments of the invention. Another non-aqueous, low-polarity solvent for use herein is the mono-, di-, tri-, or tetra-$C_2$–$C_3$ alkylene glycol mono $C_2$–$C_6$ alkyl ethers. The specific examples of such compounds include diethylene glycol monobutyl ether, tetraethylene glycol monobutyl ether, dipropoyene glycol monoethyl ether, and dipropylene glycol monobutyl ether. Butoxy-propoxy-propanol (BPP) is also contemplated as a solvent. Another type of non-aqueous, low-polarity organic solvent useful herein is the lower molecular weight polyethylene glycols (PEGs). Such materials are those having molecular weights of at least about 150. PEGs of molecular weight ranging from about 200 to 600 are most preferred. Solvents are typically utilized in the present compositions at a level of from about 0% to about 30% by weight of the composition.

A combination of a 2-alkyl alkanol and a solvent as described herein in a composition incorporated provides acceptable wetting capabilities and thus provides streak-free and evaporation benefits. "Wetting" means that the composition forms a film, instead of single droplets, when applied onto a surface, particularly a hydrophobic surface, and/or does not form droplets on said surface when drying. The formation of droplets during drying can result in visible residues ("streaks") on said surface. By contrast, the drying as a film results in the reduction or even the prevention of visible residues after drying (streak-free cleaning benefit). Furthermore, the wetting capabilities as described herein resulting in the formation of an even film of composition on the surface to which said composition has been applied.

In alternative embodiments of the invention, the compounds described above may be added to commercially available compositions, such as those available from The Procter & Gamble Company.

In an alternative embodiment of the invention, the compounds described above can be formulated into cosmetic or pharmaceutical compositions. Suitable adjunct ingredients in topical cosmetic or pharmaceutical compositions include carriers comprising one or more ingredients selected from the group consisting of i) emollients, ii) solvents, iii) humectants, iv) thickeners, v) powders, vi) perfumes, vii) waxes, viii) preservatives, ix) surfactants, x) bases, and others in addition to, or instead of, the adjunct ingredients listed above. Topical compositions that can be applied locally to the skin may be in any form including solutions, oils, creams, ointments, gels, lotions, shampoos, leave-on and rinse-out hair conditioners, milks, cleansers, moisturizers, sprays, skin patches, and the like. Typically, about 1 to about 1000, preferably about 1 to about 100 milligrams per square inch of the composition is applied to the affected area. One of ordinary skill in the art would be able to select appropriate adjunct ingredients and amounts to formulate in the compositions described above without undue experimentation, depending on the compound selected and the intended use of the composition.

Kits Comprising Compounds Provided Herein

This invention further relates to kits comprising a compound and/or composition described herein and instructions on the use of the compounds and/or compositions described herein with the packages containing the compounds and/or compositions or with other forms of advertising associated with the sale or use of the compounds and/or compositions. The instructions may be included in any manner typically used by consumer product manufacturing or supply companies. Examples include providing instructions on a label attached to the container holding the compounds and/or compositions; on a sheet either attached to the container or accompanying it when purchased; or in advertisements, demonstrations, and/or other written or oral instructions which may be connected to the purchase or use of the compounds and/or compositions.

Specifically the instructions will include a description of the use of the compounds and/or compositions. The instructions, for instance, may additionally include information relating to the recommended amount of compounds and/or compositions to apply to the substrate.

Biofilm Vial Apparatus

Referring to FIG. 1, there is shown a cross sectional view of a disposable biofilm growth apparatus for the growth and testing of biofilms on various surfaces, that includes plastic vial 6 (made of polyethylene, polytetrafluoroethylene, polyvinyl chloride, polystyrene, or other polymer, but preferably of polypropylene) containing internal projecting threads 5, into which a screw cap assembly 7 can be inserted. The screw cap assembly consists of a molded plastic top portion 1 and hollow, threaded portion 3, over which is placed an O-ring 2 (made of a silicone, a synthetic or natural rubber, or other suitable material) that provides a liquid impermeable seal when the cap assembly 7 is screwed into vial 6. Into the hollow space of the cap assembly 7 is inserted a disc 4 comprised of a surface on which a biofilm is to be grown, including, but not limited to a polymer, ceramic, metal, glass, composite, or natural surface such as wood. The disc 4 is fixed in place, either by friction, or by use of a suitable biocompatible adhesive (that does not inhibit biofilm growth) inserted into the hollow space of the cap assembly, such that the exposed disc surface is flush with the end of the threaded portion of the cap 3. Useful dimensions for the apparatus include, but are not limited to those where the hollow threaded portion 3 has an inner diameter of about 8 millimeters, the plastic vial 6 has an inner diameter of about 11 millimeters, and the disc 4 has a diameter of about 8 millimeters.

Referring to the apparatus shown in FIG. 1, a biofilm may be grown on the surface of disc 4. This may be accomplished by placing into vial 6 a volume of liquid growth medium inoculated with bacteria or fungi, screwing in cap assembly 7 having positioned therein disc 4, and placing the vial on a tissue culture rotator in an appropriate controlled temperature environment. Test compounds that are candidates for controlling biofilms can be added to the liquid growth medium before biofilm formation, added after biofilm formation, or both.

Biofilm Growth Chamber Array

An apparatus for testing biofilm control on a substrate surface is an aspect of the invention. The apparatus comprises a first body having a platform holding a removable substrate surface lacking projections, the substrate surface for growing biofilm thereon; and a second body adapted to receive the first body in alignment, the second body having a plurality of individual wells; wherein the wells are in fluid tight communication with the substrate surface of the first body when the first and second bodies are assembled and in use.

Figure 2A:
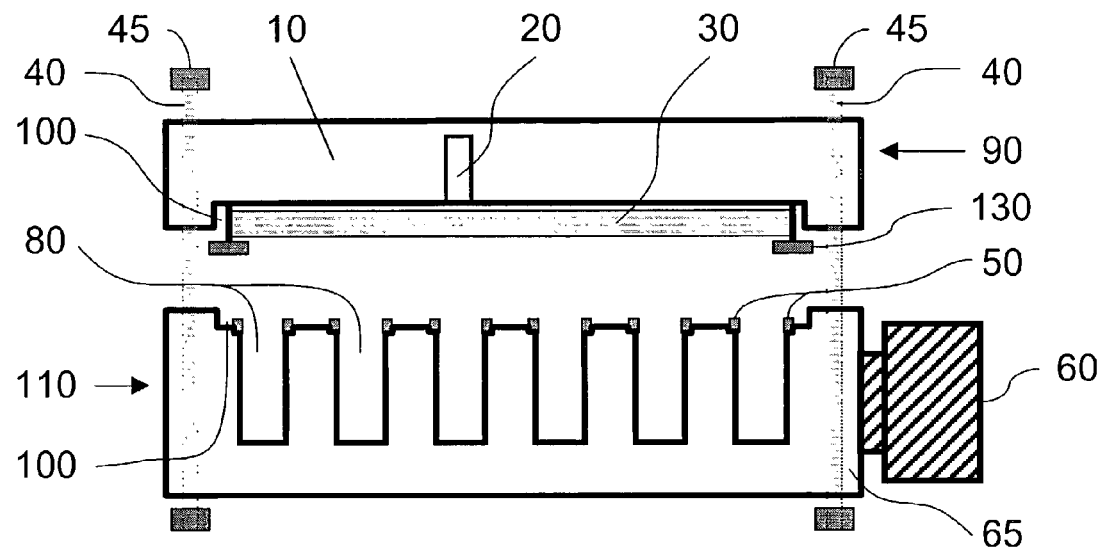
FIG. 2a is a side cross sectional view of one embodiment of the growth chamber array-based biofilm growth and test method invention described in Assay Reference Example 5.
Figure 2B:
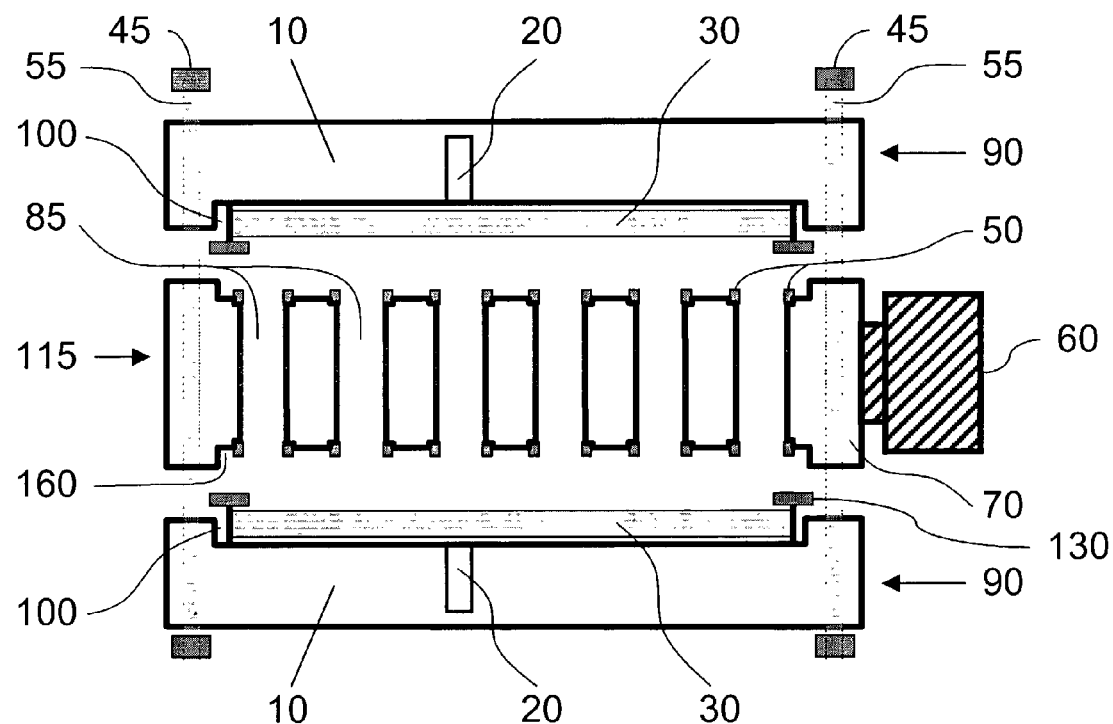
FIG. 2b is a side cross sectional view of an alternative embodiment of the growth chamber array-based biofilm growth and test method invention described in Assay Reference Example 6.

Referring to FIG. 2a, there is shown a side cross sectional view of a re-usable two-piece biofilm growth chamber array (2P-GCA), and shown in FIG. 2b is a side cross sectional view of a re-usable three-piece design (3P-GCA). Both the 2P-GCA and the 3P-GCA allow for the growth and testing of biofilms on various materials, under realistic conditions. The illustrations of the parts of the inventions shown in FIGS. 2a, 2b, 3, and 4 are not meant to be limiting, and certain simple modifications will be obvious to those skilled in the art in light of the present disclosure.

Referring to the invention depicted in FIG. 2a, the 2P-GCA includes a lid assembly 90 that may be configured to accept various materials attached to or part of a growth surface 30, and a vessel assembly 110, containing a plurality of individual growth chambers (wells), adapted to provide a fluid tight communication between individual wells 80 of the assembly and surface 30. Contact between the lid assembly 90 and vessel assembly 110 is maintained by the use of bolts 40 and nuts 45 as well as by the use of alignment pins (made preferably of stainless steel) inserted into alignment pin holes 20, wherein the fluid tight communications are maintained by the use of individual O-rings 50 (made of a silicone, a synthetic or natural rubber, or other suitable material) by using a single O-ring per well 80. When the invention is in the fully assembled configuration, O-rings 80 tightly contact both the vessel assembly 110 and the surface 30.

Referring to FIG. 2a, the lid assembly 90 is machined from a single block of polymer 10 (such as polypropylene, polyethylene, polytetrafluoroethylene, or other polymer) to include a depression 100 of such a dimension as to accept surface 30, alignment pin holes 20, holes to accommodate the surface securing screws 130, and holes to accept bolts 40. It will be obvious to those skilled in the art in light of the present disclosure that the lid assembly block could alternatively be machined from a material other than a polymer, such as a metal, composite, or other material, or preformed in a casting or molding process from almost any material desired.

Figure 3:
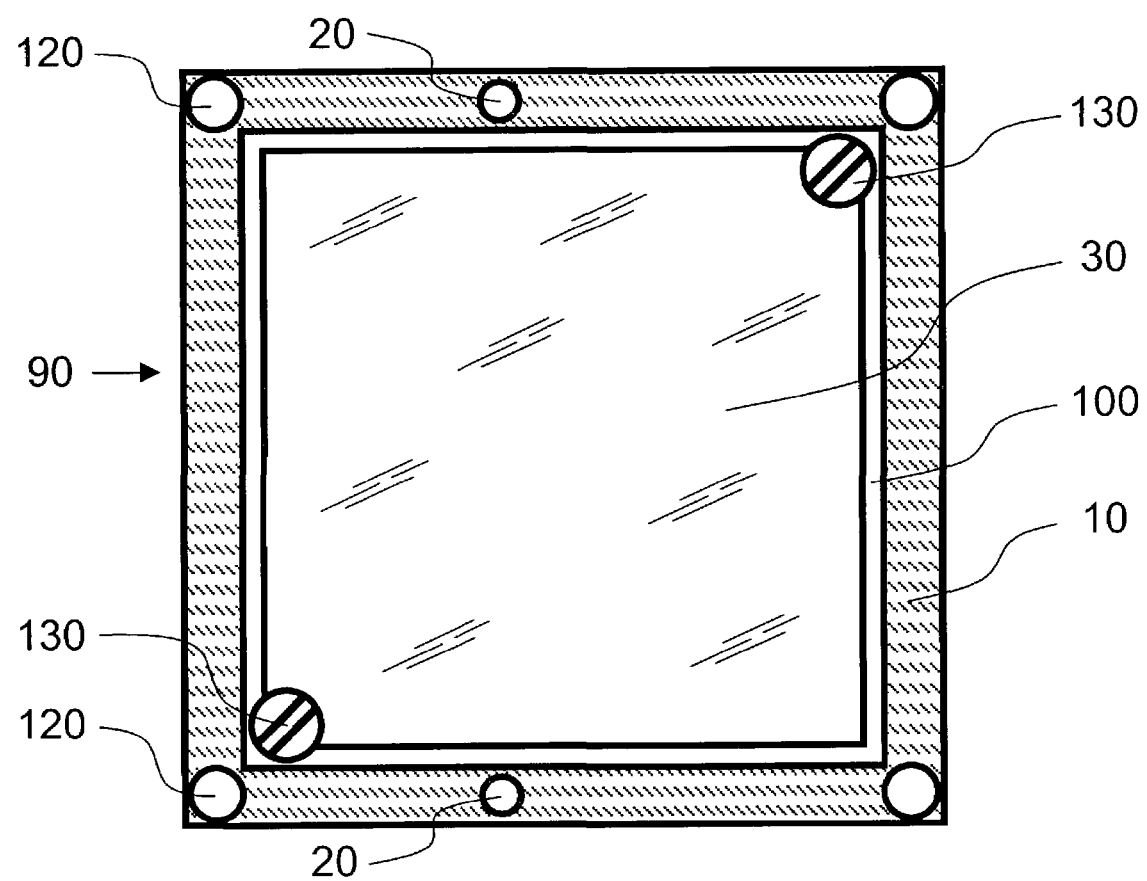
FIG. 3 is a top view of one of the two lids of the growth chamber array-based biofilm growth and test method invention described in Assay Reference Examples 5 and 6.
Figure 4:
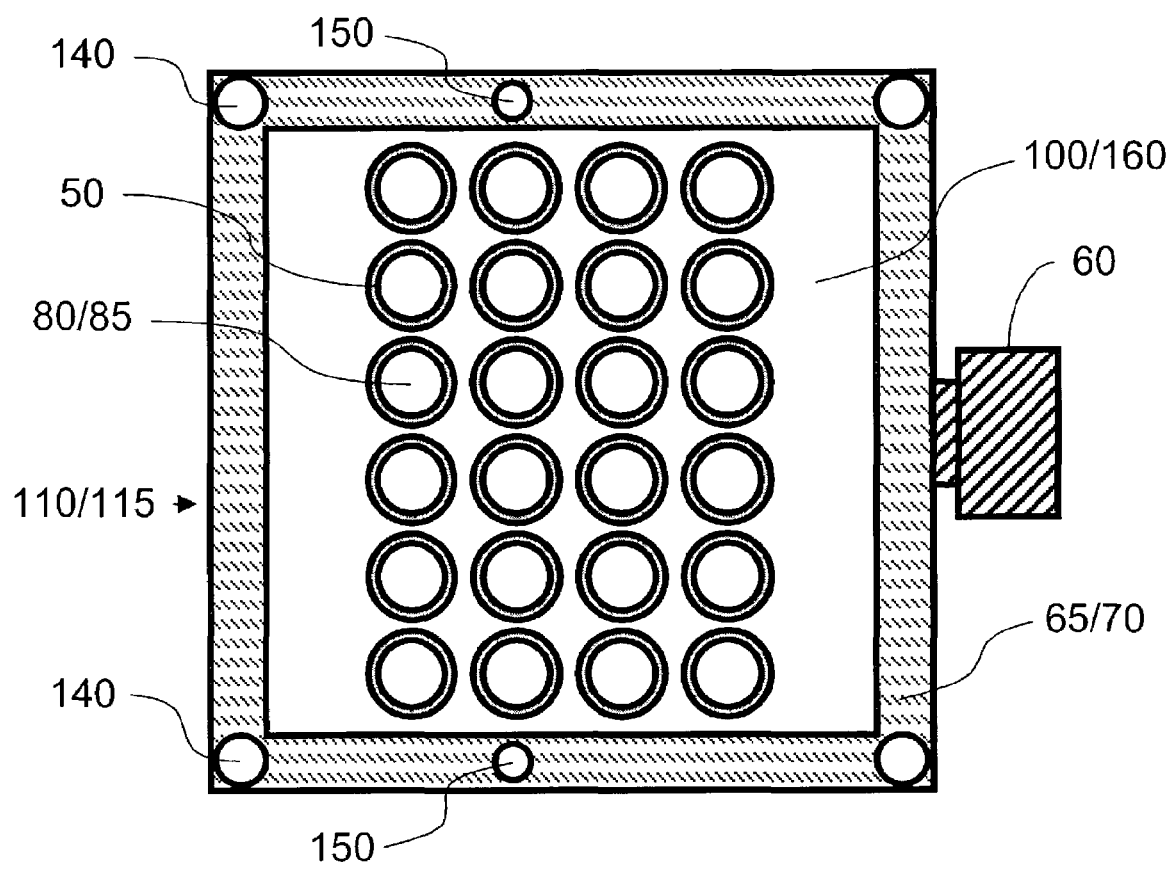
FIG. 4 is a top view of the middle piece of the growth chamber array-based biofilm growth and test method invention described in Assay Reference Examples 5 and 6.

Referring to FIG. 3 and FIG. 4, there are shown top views of lid assembly 90, and vessel assembly 110, respectively. Referring to FIG. 3, lid assembly block 10 contains depression 100, in which surface 30 is secured by use of two surface securing screws 130. In addition, it will be seen that there are included two alignment pin holes 20, intended to accept two alignment pins which assist in maintaining the alignment of the lid assembly 90 and the vessel assembly 110. In addition, four holes are intended to accept four bolts 40 that maintain the contact between the two parts 90 and 110 of the 2P-GCA. Referring to FIG. 4, the equivalent holes machined into vessel assembly block 70 may be seen, wherein the holes 140 and 150 in the vessel assembly block 70 are intended to mate with the holes 120 and 20, respectively, in the lid assembly block 10, such that continuity of bolts 40 and alignment pins that fit the alignment holes 20 is maintained.

Referring to FIG. 2a, vessel assembly 110 is also machined from a single block of polymer 65 (such as polypropylene, polyethylene, polytetrafluoroethylene, or other polymer) to include a depression 160 of such a dimension as to accept the surface 30, alignment pin holes 20, holes to accommodate the surface securing screws 130, and holes to accept bolts 40. It will be obvious to those skilled in the art in light of the present disclosure that the vessel assembly block, as for the lid assembly block, could also alternatively be machined or otherwise made from a material other than a polymer, as described above.

Referring to FIG. 4, the vessel assembly 110 of the present invention contains a plurality of individual wells 80 machined into depression 160, which is in turn machined into the vessel assembly block to receive surface 30 that projects from lid assembly 90, both referred to in FIG. 2a and FIG. 3. Each well 80 is intended to mimic an individual growth vial such as vial 6 referred to in the invention disclosed in FIG. 1, and each is machined such that an additional 0.5 to 5 millimeter depression of larger diameter than the well is included to provide a seat (receptacle) for an O-ring 50, of the type mentioned above.

Referring to FIG. 2a and FIG. 4, vessel assembly 110 includes an attachment arm 60 made of polymer or other material, that is adapted to be attached to a tissue culture rotator or similar rotational device able to smoothly rotate the fully assembled growth chamber of the present invention in a temperature controlled environment, as described for the invention disclosed in FIG. 1. Such uniform rotation allows for reproducible growth of individual, circular biofilms on the surface of interest 30.

When in use, and referring to the 2P-GCA invention shown in FIG. 2a, FIG. 3, and FIG. 4, an array of individual biofilms may be grown on a surface 30 of interest. This may be accomplished by placing O-rings 50 in their seats within vessel assembly 110, filling the individual wells 80 with the same or different volumes of the same or different liquid growth media, inoculating each well individually or together with the same or different bacteria or fungi, attaching lid assembly 90 that contains the secured surface of interest using alignment pins inserted into the alignment pin holes 20/150, securing the lid and vessel assemblies together using bolts 40 and nuts 45, and attaching the entire assembled device on a tissue culture rotator using attachment arm 60 or placing the device with the surface-of-interest side down in a shaking incubator, followed by incubation at the appropriate temperature with or without rotation or shaking, respectively.

A further apparatus for testing biofilm control on a substrate surface is an aspect of the present invention. The apparatus comprises first and third bodies, each body having a platform holding a removable substrate surface lacking projections, the substrate surface for growing biofilm thereon; and a second body having a first side and a second side, the second body adapted to receive the first and third bodies in sandwich alignment to the first side and second side, the second body having a plurality of individual openings extending from the first side to the second side providing a well open at each end and in fluid tight communication with the substrate surface of the first and third bodies when the apparatus is assembled and in use.

Referring to FIG. 2b, there is shown an alternative embodiment of the vessel assembly invention disclosed in FIG. 2a. Referring to FIG. 2b in addition to FIG. 3 and FIG. 4, it will be seen that the vessel assembly 110 is modified such that the plurality of wells 85 are machined through the entire block 70, and an additional depression 160, seats for O-rings 50, and O-rings 50 are added to result in a new vessel assembly 115. The vessel assembly 115 is thereby machined to accept two identical surfaces 30 that are attached as part of two identical lid assemblies 90.

In many respects, the 3P-GCA is identical to the 2P-GCA, except that the vessel assembly is modified to accept two identical lid assemblies 90. The four bolts 40 depicted in FIG. 2a are lengthened slightly to accommodate the larger dimension of the fully assembled three-piece assembly, resulting in the four longer bolts 55 depicted in FIG. 2b. This 3-piece embodiment has the advantage that in cases where the growth medium must be changed before the biofilm growth is complete, only one lid need be removed, hence the biofilm growing on the other lid remains completely undisturbed. In addition, in cases where the biofilm can be grown without changing the growth medium, twice as many biofilms can be formed and/or tested.

In one embodiment of both the 2P-GCA and the 3P-GCA, the depression in lid assembly 90 and vessel assembly 110/115 is machined such that the dimensions accept a standard bathroom tile as the surface 30. This arrangement has the advantage that the tile can either serve as the biofilm growth surface itself, or the tile can serve as a support for a layer of different material of interest, including, but not limited to a polymer, ceramic, metal, glass, composite, or natural surface such as wood. Such a layer can be attached to the tile with adhesive, tape, friction, or other means, and can thereby serve as the actual biofilm growth surface in the fully assembled invention.

In a bathroom tile embodiment, referring to FIG. 2a, FIG. 3, and FIG. 4, useful dimensions of the machined block 10 of the lid assembly 90 include, but are not limited to, the block size being about 156 millimeters square with a thickness of about 25 millimeters, having a depression 100 of about 109 millimeters square with a depth of about 3 millimeters. Such dimensions are sufficient to accommodate a standard bathroom tile of about 108 millimeters square. Useful dimensions of the block 65 of the vessel assembly 110 include, but are not limited to, the block size being about 156 millimeters square with a thickness of about 41 millimeters, having a depression 160 of about 109 millimeters square with a depth of about 3 millimeters, 24 holes of diameter about 8 to 12 millimeters extending to a depth of about 35 millimeters, and with about a 15 to 18 millimeter center-to-center spacing.

In a bathroom tile embodiment, referring to FIG. 2b, FIG. 3, and FIG. 4, useful dimensions include the same dimensions mentioned above, except with the vessel assembly 115 having a thickness of about 43 millimeters, an additional depression 160 of about 109 millimeters square with a depth of about 3 millimeters added on the reverse side of the block 70 to accommodate a second lid assembly 90, and the well holes 85 extending entirely through the block.

When in use, referring to the 3P-GCA invention shown in FIG. 2b, FIG. 3, and FIG. 4, an array of individual biofilms may be grown on two surfaces 30 of interest, where each of the two surfaces may be made of the same or different material. This may be accomplished in an identical manner to that mentioned above for the 2P-GCA invention, except that the lower lid assembly 90 is attached securely using the threaded bolts 65 and four of the nuts 45 before adding the volumes of liquid growth media.

In both the 2P-GCA and 3P-GCA embodiments of the invention, test compounds that control biofilms can be added to the liquid growth medium before biofilm formation, added after biofilm formation, or both. Quantification of the effects of such compounds on biofilm formation and/or dispersion is accomplished as described above. After use, surfaces 30 can be removed and discarded or cleaned and re-used, and the wells 80/85 can be easily cleaned for re-use by using a test tube brush and commonly available detergent formulations. This method is particularly suited to the study of biofilms that may be formed on hard surfaces, and their susceptibility to, for example, various cleaning compositions.

The growth chamber apparatus provided by the present invention is a reusable device where growth and assays are both carried out in the same device. There is no need for physical intervention such as breaking protrusions as in Ceri et al. (U.S. Pat. No. 6,326,190 or U.S. 20010049975), or otherwise disturbing the biofilm. The device is optimized for hard, water impermeable surfaces as substrate, however, the device is versatile in that any surface is possible as a substrate. The device is easily configurable for automation with limited or no human intervention in that a robot-removable lid may be used and all steps of addition and removal of liquids, including quantitation steps, may be automated. The device is easily scalable to higher or lower well density and/or larger or smaller wells. Aeration is controllable over a wide range by varying the volume of liquid in the wells, as well as varying the rotation speed of the rotator or shaker.

A method of screening a test compound for control of biofilm on a substrate surface, comprising obtaining the above described apparatus, incubating a biofilm forming microorganism with the test compound in a well of the apparatus under conditions that allow biofilm formation on the substrate surface absent the test compound, and comparing biofilm formation on the substrate surface in the presence of the test compound with biofilm formation on the substrate surface in the absence of the test compound is an aspect of the invention. When biofilm formation in the presence of the compound is less than in the absence of the test compound, then the test compound has inhibitory activity for biofilm formation on the substrate surface, and when biofilm formation in the presence of the compound is greater than in the absence of the test compound, then the test compound has stimulatory activity for biofilm formation on the substrate surface.

A method of screening a test compound for dispersion of an existing biofilm on a substrate surface, comprising obtaining the above described apparatus, incubating a biofilm forming microorganism in a well of the apparatus under conditions to form biofilm on the substrate surface, contacting the biofilm on the substrate surface with a test compound, and comparing biofilm amount on the substrate surface in the presence of the test compound with biofilm amount on the substrate surface in the absence of the test compound is an aspect of the invention. When biofilm amount in the presence of the compound is less than in the absence of the test compound, then the test compound has activity for biofilm dispersion on the substrate surface.

All amounts, parts, percentages and ratios used herein are expressed by weight unless otherwise specified. All U.S. Patents cited herein are hereby incorporated by reference.

Following long-standing patent law convention, the terms "a" and "an" mean "one or more" when used in this application, including the claims.

The compounds described herein can be prepared by conventional organic syntheses, readily available to one of ordinary skill in the art without undue experimentation. Specific examples are described herein below.

EXAMPLES

The following examples are illustrative of this invention, but are not meant to limit or otherwise define its scope.

Various abbreviations are used herein. Abbreviations that can be used and their definitions are shown below in Table 1.

TABLE 1

Abbreviations

| Abbreviations | Definitions |
| --- | --- |
| BOC-ON | 2-(tert-Butoxycarbonyloxyimino)-2-phenylacetonitrile |
| CV | crystal violet |
| DIEA | N,N-Diisopropylethylamine |
| EtOAc | ethyl acetate |
| g | grams |
| ISMS | Ion spray mass spectrometry |
| mg | milligrams |
| mL | milliliters |
| mmol | millimoles |
| PBS | phosphate buffered saline |
| PyBOP | Benzotriazol-1-yl-oxytripyrrolidinephosphonium hexafluorophosphate |
| TEA | Triethylamine |
| TFA | Trifluoroacetic acid |
| THF | Tetrahydrofuran |

Compound Synthesis Examples

Example 1

N-(tert-Butoxycarbonyl)-(S)-(−)-2-azetidinecarboxylic acid (1)

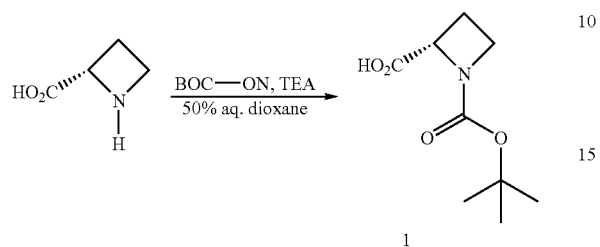

(S)-(−)-2-Azetidinecarboxylic acid (Aldrich Chemical Company, Milwaukee, Wis.) (1.00 g, 9.89 mmol) is dissolved in 12 mL of 1:1 dioxane:water. Triethylamine (2.1 mL, 14.84 mmol) is added followed by BOC-ON (2.68 g, 10.9 mmol). The mixture is stirred for 6.75 hours then poured onto water (50 mL) and extracted with ether (7 times, 50 mL each). The aqueous solution is cooled in an ice-bath and the pH adjusted to approximately 2.5 with ice-cold 1N HCl solution. The resulting solution is extracted with methylene chloride (3 times, 50 mL each). The combined organic extracts are dried over $MgSO_4$, filtered and concentrated in vacuo to afford an oil. Hexane (100 mL) is added to this oil and the mixture placed in the freezer overnight. The hexane is decanted and the product (1) dried under vacuum to afford a white solid. ISMS: $MH^+$ 202.2

Example 2

N-(tert-Butoxycarbonyl)-(S)-(−)-2-azetidinecarboxylic acid n-decyl amide (285)

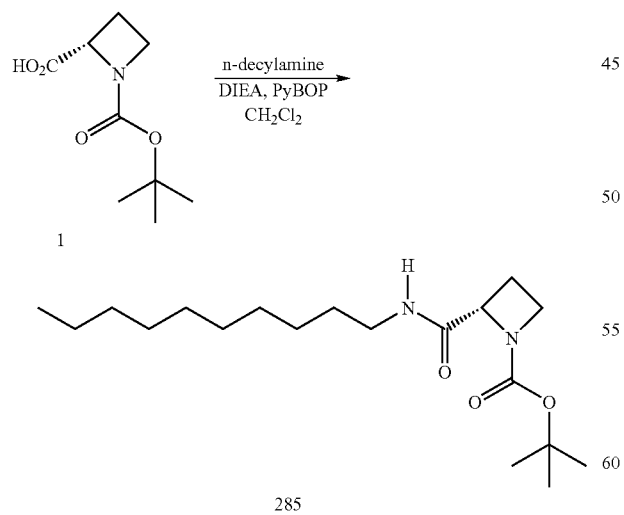

N-(tert-Butoxycarbonyl)-(S)-(−)-2-azetidinecarboxylic acid (1) (90 mg; 0.447 mmol) is dissolved in methylene chloride (3 mL) at ambient temperature. n-Decylamine (72 mg; 0.470 mmol), N,N-diisopropylethylamine (116 mg; 0.895 mmol) and PyBOP (244 mg; 0.470 mmol) are added sequentially. The reaction is stirred for 4 days at room temperature, then concentrated under reduced pressure. The crude product is purified via silica gel chromatography using a gradient elution (10%→60% ethyl acetate in hexanes) affording the desired product (285). ISMS: $MH^+$ 341.4

Compounds 283, 284 and 286 are prepared in a similar manner using n-hexylamine, n-octylamine and n-dodecylamine, respectively, in place of n-decylamine.

Example 3

(S)-(−)-2-azetidinecarboxylic acid n-decyl amide (289)

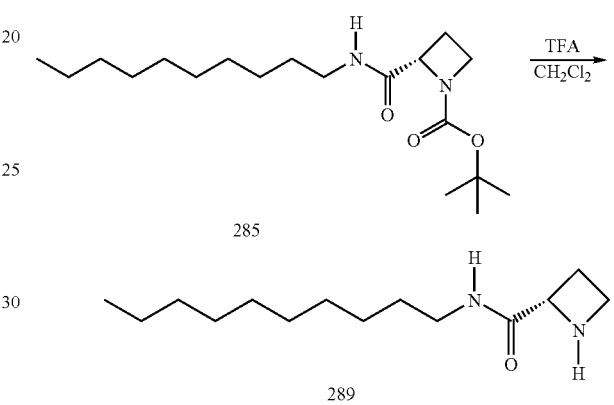

N-(tert-Butoxycarbonyl)-(S)-(−)-2-azetidinecarboxylic acid n-decyl amide (285) (160 mg; 0.470 mmol) is dissolved in methylene chloride (4 mL) at ambient temperature. Trifluoroacetic acid (2 mL) is added and the solution is stirred for 2 hours at ambient temperature. The solution is concentrated in vacuo at 40° C. The residue is dissolved in methylene chloride (20 mL) and poured onto saturated sodium bicarbonate solution. The pH is adjusted to 9 with saturated potassium carbonate solution. The mixture is shaken and the layers separated. The water layer is extracted with methylene chloride (3 times, 5 mL each). The combined organic extracts are washed with water, dried over $MgSO_4$, filtered, and concentrated in vacuo affording the desired product (289) as a solid. ISMS: $MH^+$ 241.2

Compounds 287, 288, and 290 are prepared in a similar manner from compounds 283, 284 and 286, respectively.

Example 4

N-(Acetyl)-DL-proline n-decyl amide (7)

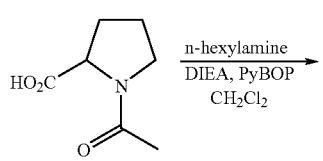

-continued

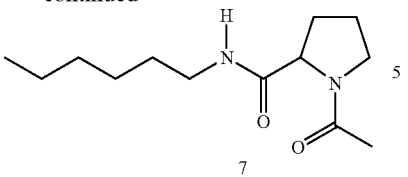

7

N-(Acetyl)-DL-proline (Sigma Chemical Company, St. Louis, Mich.) (100 mg; 0.64 mmol) is dissolved in methylene chloride (3 mL) at ambient temperature. n-Hexylamine (77 mg; 0.76 mmol), N,N-diisopropylethylamine (181 mg; 1.40 mmol) and PyBOP (397 mg; 0.76 mmol) are added sequentially. The reaction is stirred for 18 hours at room temperature, then concentrated under reduced pressure. The residue is purified via silica gel chromatography using a gradient elution (80%→100% ethyl acetate in hexanes, followed by 50%→100% acetone in hexanes) affording the desired product (7). ISMS: $MH^+$ 241.4

Compounds 8 and 9 are prepared in a similar manner using n-octylamine and n-decylamine, respectively, in place of n-hexylamine.

Example 5

N-(tert-Butoxycarbonyl)-L-proline n-decyl amide (12)

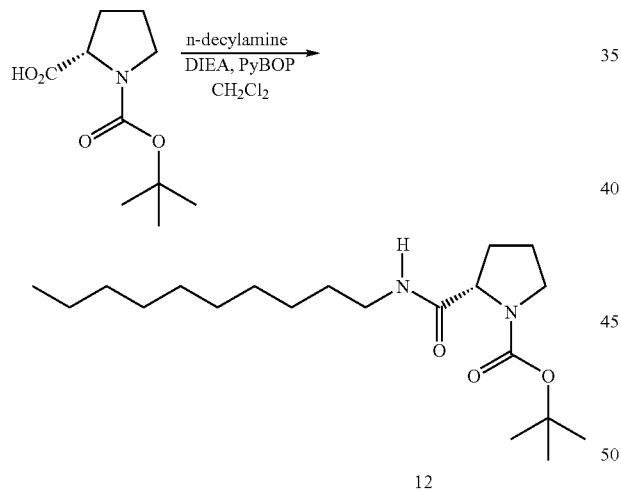

12

N-(tert-butoxycarbonyl)-L-proline (Aldrich Chemical Company, Milwaukee, Wis.) (137 mg; 0.64 mmol) is dissolved in methylene chloride (3 mL) at ambient temperature. n-Decylamine (120 mg; 0.76 mmol), N,N-diisopropylethylamine (181 mg; 1.40 mmol) and PyBOP (397 mg; 0.76 mmol) are added sequentially. The reaction is stirred for 42 hours at room temperature, then concentrated under reduced pressure. The residue is purified via silica gel chromatography using a gradient elution (20%→70% ethyl acetate in hexanes) affording the desired product (12) as an oil. ISMS: $MH^+$ 355.2

Compounds 10, 11, 155 and 160 are prepared in a similar manner using n-hexylamine, n-octylamine, n-butylamine and n-dodecylamine, respectively, in place of n-decylamine.

Compounds 153, 154, 158, 152 and 159 are prepared in a similar manner to compounds 10, 11, 12, 155 and 160, respectively, using N-(tert-butoxycarbonyl)-D-proline in place of N-(tert-butoxycarbonyl)-L-proline.

Example 6

L-proline n-decyl amide (32)

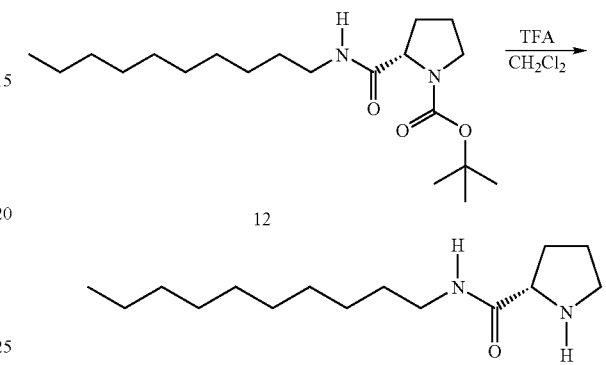

N-(tert-Butoxycarbonyl)-L-proline n-decyl amide (12) (120 mg; 0.339 mmol) is dissolved in methylene chloride (4 mL) at ambient temperature. Trifluoroacetic acid (2 mL) is added and the solution is stirred for 2.5 hours at ambient temperature. The solution is concentrated in vacuo at 40° C. The residue is dissolved in methylene chloride (20 mL) and poured onto saturated sodium bicarbonate solution. The pH is adjusted to 9 with saturated potassium carbonate solution. The mixture is shaken and the layers separated. The water layer is extracted with methylene chloride (3 times, 5 mL each). The combined organic extracts are washed with water, dried over $MgSO_4$, filtered, and concentrated in vacuo affording the desired product (80 mg) as an oil. ISMS: $MH^+$ 254.8

Compounds 30, 31, 165 and 168 are prepared in a similar manner from compounds 10, 11, 155 and 160, respectively.

Compounds 163, 164, 166, 162 and 167 are prepared in a similar manner from compounds 153, 154, 158, 152 and 159, respectively.

Example 7

(R)-(+)-1-(tert-Butoxycarbonyl)-2-piperidinecarboxylic acid n-octyl amide (22)

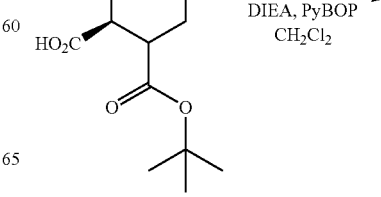

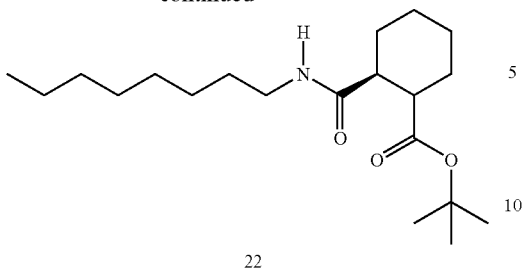

(R)-(+)-1-(tert-Butoxycarbonyl)-2-piperidinecarboxylic acid (Aldrich Chemical Company, Milwaukee, Wis.) (1.00 g; 4.36 mmol) is dissolved in methylene chloride (20 mL) at ambient temperature. n-Octylamine (0.620 g; 4.80 mmol), N,N-diisopropylethylamine (1.24 g; 9.60 mmol) and PyBOP (2.50 g; 4.80 mmol) are added sequentially. The reaction is stirred for 25 hours at room temperature, then concentrated under reduced pressure. The residue is purified via silica gel chromatography using a gradient elution (20%→40% ethyl acetate in hexanes) affording the desired product (22) as an oil. ISMS: MH+341.2

Compound 19 is prepared in similar manner using (S)-(−)-1-(tert-butoxycarbonyl)-2-piperidinecarboxylic acid (Aldrich Chemical Company, Milwaukee, Wis.) in place of (R)-(+)-1-(tert-butoxycarbonyl)-2-piperidinecarboxylic acid.

Example 8

(R)-(+)-2-piperidinecarboxylic acid n-octyl amide (23)

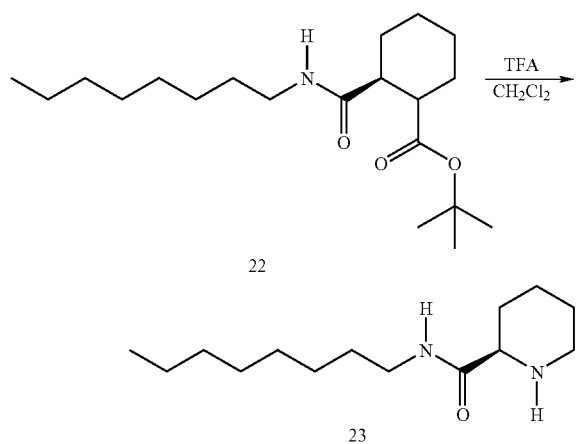

(R)-(+)-1-(tert-Butoxycarbonyl)-2-piperidinecarboxylic acid n-octyl amide (8) (1.00 g; 2.94 mmol) is dissolved in methylene chloride (40 mL) at ambient temperature. Trifluoroacetic acid (20 mL) is added and the solution is stirred for 7 hours at ambient temperature. The solution is concentrated in vacuo at 40° C. The residue is dissolved in methylene chloride (200 mL) and poured onto saturated sodium bicarbonate solution. The pH is adjusted to 9 with saturated potassium carbonate solution. The mixture is shaken and the layers separated. The water layer is extracted with methylene chloride (3 times, 50 mL each). The combined organic extracts are washed with water, dried over MgSO4, filtered, and concentrated in vacuo affording the desired product (23) as a solid. ISMS: MH+ 240.8

Compound 20 is prepared in a similar manner from compound 19.

Example 9

1-Octanoyl-(R)-(+)-2-piperidinecarboxylic acid n-octyl amide (28)

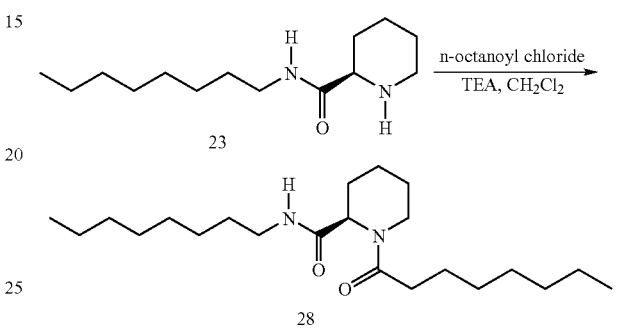

(R)-(+)-2-piperidinecarboxylic acid n-octyl amide (23) (100 mg; 0.416 mmol) is dissolved in methylene chloride (3 mL) at ambient temperature. Triethylamine (63 mg; 0.624 mmol) is added and the solution cooled in an ice-bath. Octanoyl chloride (74 mg; 0.458 mmol) is added dropwise via syringe. The solution is stirred for 15 minutes and then allowed to warm to ambient temperature. After stirring for an additional 4.5 hours, the solution is poured onto saturated sodium bicarbonate solution and extracted with methylene chloride (20 mL). The methylene chloride extract is washed with water, dried over MgSO4, filtered, and concentrated in vacuo. The residue is purified via silica gel chromatography using a gradient elution (0%→40% ethyl acetate in hexanes) affording the desired product (28) as an oil. ISMS: MH+367.4

Compounds 21 and 24 are prepared in a similar manner from compounds 20 and 23, respectively, using acetyl chloride in place of octanoyl chloride.

Example 10

(S)-(−)-1-(tert-Butoxycarbonyl)-2-azepanecarboxylic acid n-octyl amide (2)

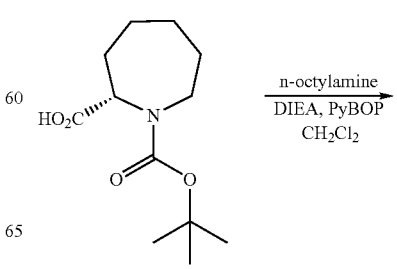

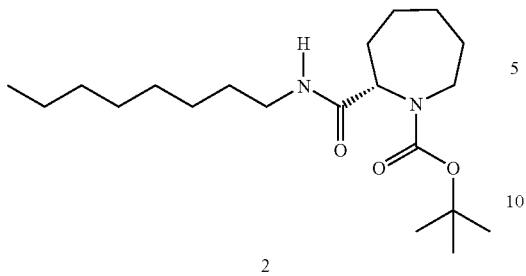

2

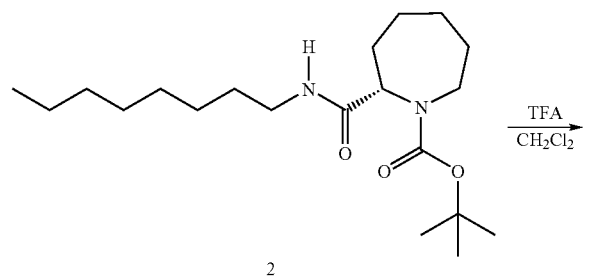

3

(S)-(−)-1-(tert-Butoxycarbonyl)-2-azepanecarboxylic acid (prepared as described in *Tetrahedron Letters* (1994), 35(2), 237–240) (1.00 g; 4.11 mmol) is dissolved in methylene chloride (20 mL) at ambient temperature. n-Octylamine (0.584 g; 4.52 mmol), N,N-diisopropylethylamine (1.17 g; 9.04 mmol) and PyBOP (2.35 g; 4.52 mmol) are added sequentially. The reaction is stirred for 24 hours at room temperature, then concentrated under reduced pressure. The residue is purified via silca gel chromatography affording the desired product (2).

Example 11

(S)-(−)-2-azepanecarboxylic acid n-octyl amide (3)

(S)-(−)-1-(tert-Butoxycarbonyl)-2-azepanecarboxylic acid n-octyl amide (2) (1.00 g; 2.82 mmol) is dissolved in methylene chloride (40 mL) at ambient temperature. Trifluoroacetic acid (20 mL) is added and the solution is stirred for 7 hours at ambient temperature. The solution is concentrated in vacuo at 40° C. The residue is dissolved in methylene chloride (200 mL) and poured onto saturated sodium bicarbonate solution. The pH is adjusted to 9 with saturated potassium carbonate solution. The mixture is shaken and the layers separated. The water layer is extracted with methylene chloride (3 times, 50 mL each). The combined organic extracts are washed with water, dried over MgSO$_4$, filtered, and concentrated in vacuo affording the desired product (3).

Example 12

N-(tert-Butoxycarbonyl)-D-proline 1,12-diaminododecane bisamide (225)

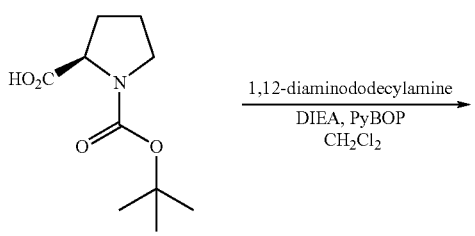

-continued

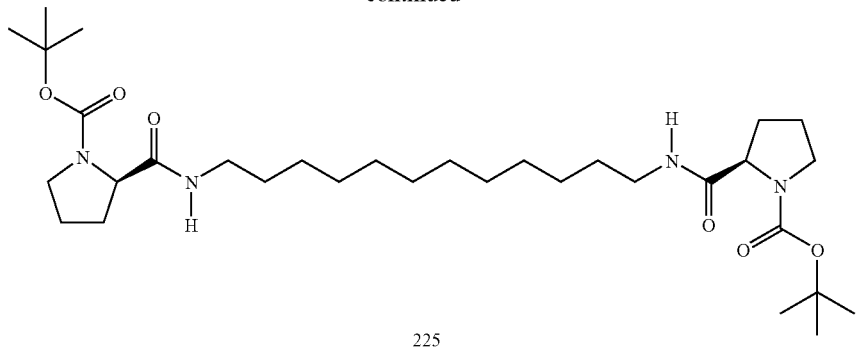

225

N-(tert-butoxycarbonyl)-D-proline (Aldrich Chemical Company, Milwaukee, Wis.) (161 mg; 0.749 mmol) is dissolved in methylene chloride (3 mL) at ambient temperature. 1,12-Diaminododecane (75 mg; 0.374 mmol), N,N-diisopropylethylamine (155 mg; 1.20 mmol) and PyBOP (409 mg; 0.786 mmol) are added sequentially. The reaction is stirred for 7 hours at room temperature, then concentrated under reduced pressure. The residue is purified via silica gel chromatography using a gradient elution (20%→50% ethyl acetate in hexanes) affording the desired product (225). ISMS: MH$^+$ 595.6

Example 13

D-proline 1,12-diaminododecane bisamide (226)

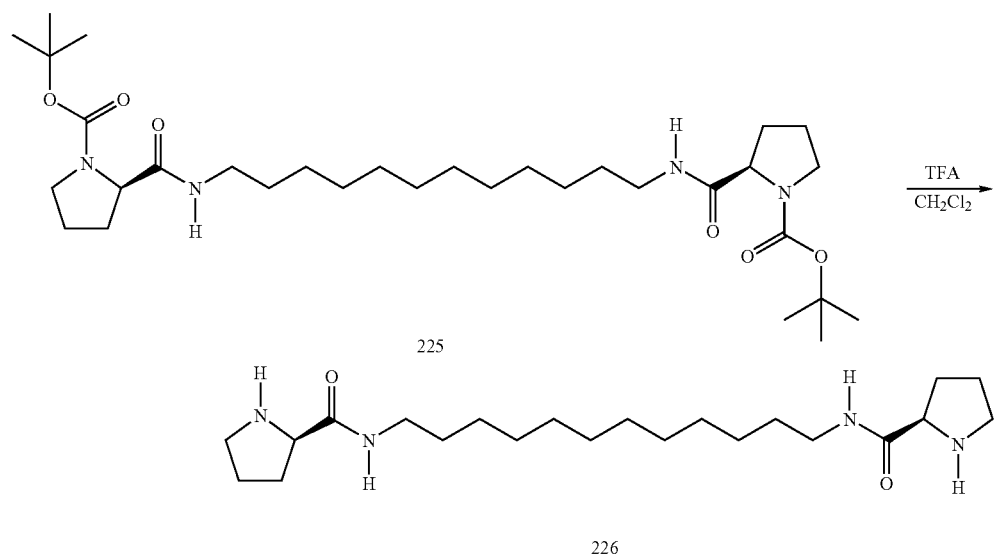

N-(tert-Butoxycarbonyl)-D-proline 1,12-diaminododecane bisamide (225) (190 mg; 0.319 mmol) is dissolved in methylene chloride (4 mL) at ambient temperature. Trifluoroacetic acid (1 mL) is added and the solution is stirred for 1.75 hours at ambient temperature. The solution is concentrated in vacuo at 40° C. The residue is dissolved in methylene chloride (20 mL) and poured onto saturated sodium bicarbonate solution. The pH is adjusted to 9 with saturated potassium carbonate solution. The mixture is shaken and the layers separated. The water layer is extracted with methylene chloride (3 times, 5 mL each). The combined organic extracts are washed with water, dried over MgSO$_4$, filtered, and concentrated in vacuo affording the desired product (226) as a solid. ISMS: MH$^+$ 395.4

ASSAY REFERENCE EXAMPLES

Primary, High-Throughput, Microplate Screening Methods

The high-throughput screening methods described are based on the ability of bacteria to adhere to and form biofilms on 96-well microplates made of polystyrene (PS), polyvinyl chloride (PVC), polypropylene (PP), or other materials, and on their ability to be stained with a dye such as crystal violet (CV) that stains the biofilms but does not stain the plastic, followed by ethanolic extraction of the dye and spectrophotometric quantitation using a microplate reader.

Various versions of such screens have been well described for several bacterial species (see, for example, Cowan, M. M., and Fletcher, M., 1987, *J. Microbiol. Methods* 7:241–249; Shea, C., and Williamson, J. C., 1990, *Biotechniques* 8:610–611; O'Toole, G. A., and Kolter, R., 1998, *Mol. Microbiol*. 28:449–461; Loo, C. Y. et al., 2000, *J. Bacteriol*. 182:1374–1382); almost any bacterium can be used. The screens can also be modified for similar use with fungi such as yeasts, by choosing optimal dyes and growth media.

This invention relates to improved screens that are easy, rapid, and are designed to facilitate automation. They can be used to discover compounds that inhibit or enhance the formation of biofilms, or additionally to discover compounds that initiate dispersion of biofilms. The screening methods can also be used to determine the susceptibility of bacteria present in biofilms to biocides or other antimicrobials.

Reference Example 1

Biofilm Prevention Screen to Screen for Compounds that Inhibit Formation of Biofilms Overnight cultures of 3 mL are made of *P. aeruginosa* strain PAO1 (grown in R2A medium (*Handbook of Microbiological Media*; CRC Press, 1997, second edition, R. M. Atlas, ed.), modified to omit $Mg^{2+}$ but to include 0.3–0.5% fructose (pH 7.0) and 3 μM ferrous ammonium sulfate), *P. fluorescens* strain ATCC 13525 (grown in R2A modified to omit $Mg^{2+}$ but to include 0.3–0.5% sodium pyruvate (pH 7.0)), *S. epidermidis* strain ATCC 35984 (grown in a ¼ dilution of TSB (*Handbook of Microbiological Media*; CRC Press, 1997, second edition, R. M. Atlas, ed.) supplemented with 1% fructose (pH 7.0) and 3 μM ferrous ammonium sulfate). To each type of growth medium, HEPES (pH 7.3) is optionally added to a final concentration of 10 mM.

To PS, PVC, or PP (preferably PP or PVC) round-bottom, 96-well microplates containing 100 μl per well of the respective growth medium as described above, compounds to be tested (dissolved in DMSO) are added and mixed, to give a final concentration of 250–500 μM. These microplates then also are used to make successive dilutions of the compounds in the same respective growth medium to yield microplates containing final concentrations of, for example, 160 μM and 32 μM of the same set of compounds. Control wells are included in the dilution series that contain only DMSO. From the 3 ml overnight cultures, each of the three dilution plate sets is inoculated with 5 μl per well of a 1:1 dilution in the same liquid growth media of the appropriate culture. The covered plate is then incubated with shaking, at 30° C. (for *P. aeruginosa* or *P. fluorescens*) or 37° C. (for *S. epidermidis*), at 200 rpm, for 16–26 hours, in a humidity controlled environment.

Cells present in biofilm attached to the microplate surface are stained with CV either after removal of the liquid from each well, followed by rinsing three times (aspiration and addition) with 150 μl per well phosphate buffered saline solution (PBS) and final addition of 100 μl per well of PBS, or by direct addition of stain to bacterial cultures without rinsing. To 100 μl per well of PBS or of bacterial culture, 25 μl/well of 1% CV solution (in ~10% ethanol) is added. After incubation at room temperature for 45 minutes, the dye solution is removed from the plates. Residual dye is immediately removed by gentle rinsing with a stream of deionized water by filling and inverting the plates 4–5 times, or by using an automated pipettor. Rinsed plates are air-dried at room temperature for 0.5–2 hours. Bound dye is extracted by the addition of 150 μL per well of 95% ethanol, followed by vigorous mixing for 10–15 seconds and incubation for 45 minutes at room temperature without shaking. Subsequently, either undiluted or diluted (in ethanol) samples of extracted CV are transferred to flat bottom, polystyrene microtiter plates and absorbances at 586 nm were measured in a microplate reader. Readings from wells containing compounds are compared to the average of data from control wells that contain only DMSO. Replicate samples are measured, and results are reported as averages of the replicate well data points.

Table 2 shows the results of this biofilm prevention screen carried out using the compounds described herein, run against biofilms of the three bacterial species specified in Reference Example 1. Data are expressed in terms of the average percentage reduction of biofilm formed in the presence of each compound, relative to the DMSO controls, for quadruplicate samples. Assays are run using the three compound concentrations indicated. Positive numbers indicate prevention of biofilm formation by a compound, and negative numbers indicate enhancement of biofilm formation by a compound (percentage coefficients of variation are ≦10%). This table clearly shows the efficacy of certain compounds in the prevention of biofilm formation on one or more bacterial species.

TABLE 2

| Cmpd. # | Structure | P. aeruginosa 390 μM | P. aeruginosa 160 μM | P. aeruginosa 32 μM | P. fluorescens 390 μM | P. fluorescens 160 μM | P. fluorescens 32 μM | S. epidermidis 390 μM | S. epidermidis 160 μM | S. epidermidis 32 μM |
|---|---|---|---|---|---|---|---|---|---|---|
| 7 | | −13% | −20% | −13% | −32% | −30% | −11% | −11% | 6% | −10% |
| 8 | | −9% | −11% | −9% | −24% | −26% | −12% | −32% | −22% | −13% |
| 9 | | −26% | −4% | −6% | 0% | −9% | −6% | 33% | −69% | −21% |
| 10 | | −16% | −16% | −7% | −6% | −5% | −1% | −25% | −17% | −18% |

TABLE 2-continued

| Cmpd. # | Structure | P. aeruginosa 390 μM | P. aeruginosa 160 μM | P. aeruginosa 32 μM | P. fluorescens 390 μM | P. fluorescens 160 μM | P. fluorescens 32 μM | S. epidermidis 390 μM | S. epidermidis 160 μM | S. epidermidis 32 μM |
|---|---|---|---|---|---|---|---|---|---|---|
| 11 | | −15% | −18% | −6% | −26% | −6% | −4% | 37% | −60% | 10% |
| 12 | | −32% | −45% | 6% | −37% | −42% | −16% | 31% | −2% | −21% |
| 19 | | −17% | −2% | 10% | 10% | 8% | 6% | −11% | −33% | −11% |
| 20 | | 15% | −22% | −16% | 40% | −14% | −16% | −59% | 1% | 1% |

TABLE 2-continued

| Cmpd. # | P. aeruginosa | | P. fluorescens | | | S. epidermidis | | | Structure |
|---|---|---|---|---|---|---|---|---|---|
| | 390 µM | 160 µM | 32 µM | 390 µM | 160 µM | 32 µM | 390 µM | 160 µM | 32 µM | |
| 21 | -11% | -12% | -6% | 20% | 4% | 2% | -24% | -23% | -15% | |
| 22 | -6% | -8% | 0% | 25% | 27% | 3% | 3% | -17% | -6% | |
| 23 | -3% | -31% | -5% | 21% | -13% | -23% | -36% | 15% | -1% | |
| 24 | -11% | -22% | -12% | -2% | -6% | -1% | -53% | -20% | -8% | |
| 28 | -9% | -3% | 0% | 26% | 38% | 21% | -51% | -44% | -5% | |

TABLE 2-continued

| Cmpd. # | Structure | P. aeruginosa 390 μM | 160 μM | 32 μM | P. fluorescens 390 μM | 160 μM | 32 μM | S. epidermidis 390 μM | 160 μM | 32 μM |
|---|---|---|---|---|---|---|---|---|---|---|
| 30 | | 18% | 9% | 2% | 19% | 11% | 11% | −6% | −7% | −12% |
| 31 | | −44% | −125% | −37% | 52% | 5% | 3% | −27% | −1% | −7% |
| 32 | | 22% | −43% | −15% | 95% | 55% | 9% | 97% | 100% | −3% |
| 152 | | 2% | −9% | −4% | −7% | 5% | 5% | −8% | −13% | −5% |
| 153 | | −4% | −6% | −9% | −3% | 4% | 7% | −17% | −7% | −8% |

TABLE 2-continued

| Cmpd. # | P. aeruginosa 390 µM | P. aeruginosa 160 µM | P. aeruginosa 32 µM | P. fluorescens 390 µM | P. fluorescens 160 µM | P. fluorescens 32 µM | S. epidermidis 390 µM | S. epidermidis 160 µM | S. epidermidis 32 µM | Structure |
|---|---|---|---|---|---|---|---|---|---|---|
| 154 | −15% | −9% | −1% | 11% | 10% | 4% | 52% | −42% | −16% | |
| 155 | 6% | 2% | −5% | 4% | 4% | 10% | 21% | −1% | −3% | |
| 158 | −40% | −34% | 1% | −40% | −11% | 3% | 54% | 52% | −10% | |
| 159 | −50% | −38% | −9% | −13% | −3% | −1% | −3% | −20% | −9% | |

TABLE 2-continued

| Cmpd. # | P. aeruginosa | | P. fluorescens | | | S. epidermidis | | | Structure |
|---|---|---|---|---|---|---|---|---|---|
| | 390 μM | 160 μM | 32 μM | 390 μM | 160 μM | 32 μM | 390 μM | 160 μM | 32 μM | |
| 160 | −59% | −44% | −2% | −18% | 0% | −1% | 29% | 20% | −9% | |
| 162 | −9% | −13% | −9% | 11% | 1% | 7% | −47% | −8% | −4% | |
| 163 | 46% | 22% | 1% | 22% | 6% | 5% | −10% | −5% | −3% | |
| 164 | 12% | 11% | 6% | 54% | 7% | 8% | −35% | −1% | −8% | |
| 165 | 1% | −16% | 2% | 20% | 4% | 10% | −12% | −15% | −6% | |
| 166 | 96% | 22% | 10% | 98% | 57% | 0% | 101% | 100% | 13% | |

TABLE 2-continued
| Cmpd. # | P. aeruginosa | | | P. fluorescens | | | S. epidermidis | | | Structure |
|---|---|---|---|---|---|---|---|---|---|---|
| | 390 μM | 160 μM | 32 μM | 390 μM | 160 μM | 32 μM | 390 μM | 160 μM | 32 μM | |
| 167 | 93% | 49% | 4% | 92% | 95% | 38% | 99% | 100% | 40% | 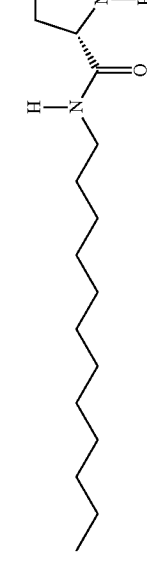 |
| 168 | 91% | 53% | 3% | 93% | 97% | 26% | 98% | 100% | 101% | 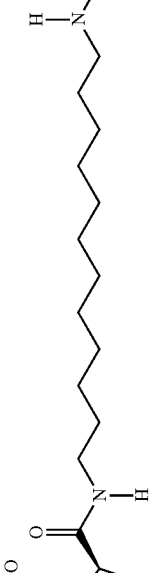 |
| 225 | −8% | 7% | 11% | −14% | 0% | 14% | −39% | −24% | −21% | 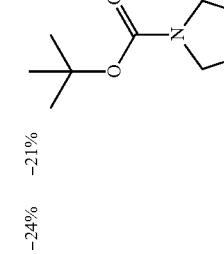 |
| 226 | 95% | 96% | −23% | 69% | 10% | −19% | 100% | 101% | 24% | 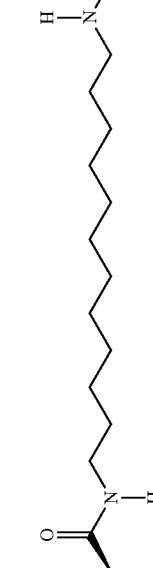 |

TABLE 2-continued

| Cmpd. # | P. aeruginosa | | P. fluorescens | | | S. epidermidis | | | Structure |
|---|---|---|---|---|---|---|---|---|---|
| | 390 μM | 160 μM | 32 μM | 390 μM | 160 μM | 32 μM | 390 μM | 160 μM | 32 μM | |
| 283 | 0% | −10% | −7% | 13% | −1% | 3% | −23% | −10% | −3% | |
| 284 | −12% | −10% | 2% | −2% | 21% | 4% | 56% | −33% | −4% | |
| 285 | −21% | −20% | 7% | −32% | −44% | −12% | 66% | 17% | 2% | |
| 286 | −54% | −22% | −5% | −98% | −60% | −9% | 12% | −29% | −15% | |

TABLE 2-continued
| Cmpd. # | P. aeruginosa | | P. fluorescens | | | S. epidermidis | | | Structure |
|---|---|---|---|---|---|---|---|---|---|
| | 390 µM | 160 µM | 32 µM | 390 µM | 160 µM | 32 µM | 390 µM | 160 µM | 32 µM | |
| 287 | −2% | 11% | −1% | 40% | −7% | −42% | 101% | 101% | 74% | 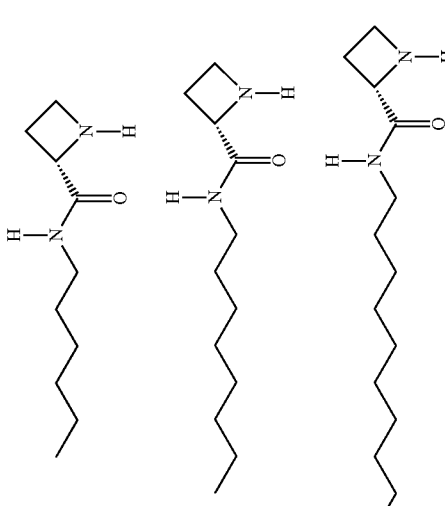 |
| 288 | 96% | 97% | 12% | 59% | 40% | −14% | 99% | 101% | 101% | 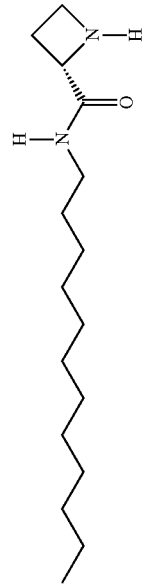 |
| 289 | 77% | −2% | 9% | 99% | 45% | −8% | 101% | 101% | 39% | 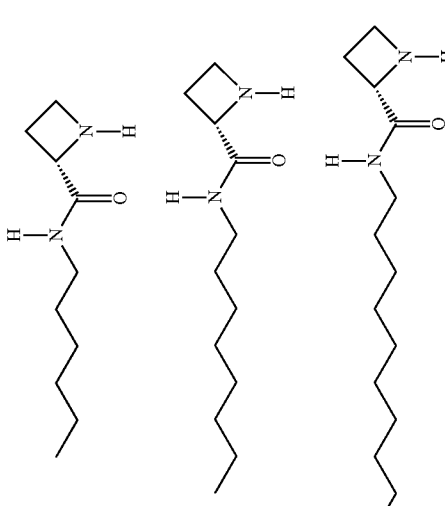 |
| 290 | 37% | −16% | 6% | 93% | 98% | −12% | 97% | 100% | 101% | 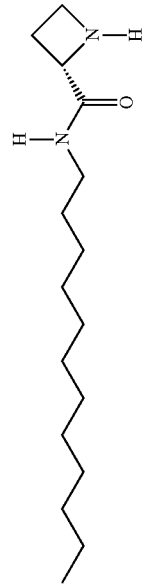 |

Reference Example 2

Biofilm Dispersion Screen to Screen for Compounds that Initiate or Facilitate Dispersion of Already-formed Biofilms Overnight cultures are made and 100 μL of growth media dispensed, as in Reference Example 1, but neither compounds nor DMSO are added, prior to inoculation of bacteria and growth using the conditions specified in Reference Example 1.

After growth of biofilm in the wells, the liquid is removed from each well, followed by rinsing once with 150 μL per well of PBS, and final liquid removal. Dilutions of compounds are either made in a separate microplate using the same method as described in Reference Example 1 (but using 100–150 μL volumes per well of PBS instead of growth media), followed by addition to the rinsed wells containing grown biofilm, or compounds are added directly to 100–150 μL volumes of PBS that is added to each well. Microplates are then incubated at 20–25° C., with or without shaking at 200 rpm, for 0.5–24 hours, followed by staining with CV, as described in Reference Example 1. Optionally, prior to staining and measurement, plates are additionally rinsed once with 150 μL of PBS, followed by addition of 1–100 mM sodium hydroxide solution and incubation at 20–25° C. for 15–60 minutes. Staining with CV and measurement are then completed as described in Reference Example 1. This optional secondary treatment loosens biofilm and allows for improved sensitivity of the screen to compound action when using bacterial biofilms that are recalcitrant to removal.

Reference Example 3

Improved Biofilm Dispersion Screen to Screen for Compounds that Initiate or Facilitate Dispersion of Already-formed Biofilms A modification of method disclosed in Reference Example 2, which greatly improves the sensitivity and reproducibility of the dispersion screen is hereby disclosed. The method is, in part, based on the observation that nutrient-deprived biofilms, such as those treated with compounds in PBS as in Reference Example 2, are inherently unstable, hence tend to generate larger numbers of false positive results in the biofilm dispersion assay. In the modification described herein, compounds are added in the presence of the fresh liquid growth media, such that the resultant biofilms continue to grow, unless a test compound triggers their dispersion.

Overnight cultures are made as above, and 100 μL of the appropriate liquid growth media are dispensed into duplicate 96 well microplates—in this fashion, two identical microplates are set up for each bacterial species to be assayed. Neither compounds nor DMSO are added prior to the inoculation of bacteria, and growth in the duplicate plates for 24 hours is allowed using the conditions specified in Reference Example 1.

After growth of biofilm to be tested in the wells, cells present in biofilm attached to one of the duplicate microplates is stained with CV, quantitated as described in Reference Example 1, and the data for the entire plate averaged, resulting in a growth control value, $t_0$. The remaining replicate of each microplate pairs is treated with compounds in DMSO, or DMSO alone for control wells, by first removing the cell suspensions from the wells, then adding fresh 100 μL volumes of the same appropriate liquid growth media, followed by direct addition and mixing of the compound DMSO solutions to give final compound concentrations of 390 μM. Incubation of the compound-containing microplates is then continued for an additional 22–26 hours using the same conditions described in Reference Example 1. Cell suspensions are then removed, 100 μL per well of a 0 mM NaOH (*S. epidermidis*), 20 mM NaOH (*P. fluorescens*), or 30 mM NaOH (*P. aeruginosa*) solution in PBS is added, and incubation at room temperature is allowed for 30 minutes. No addition of NaOH is made to the *S. epidermidis* suspension since a test assay indicated no amplification by base with *S. epidermidis*. The microplates are subsequently rinsed three times with 150 μL per well of PBS, followed by final liquid removal, staining with CV and quantitation as described in Reference Example 1. Data for each well that contained compound result in a compound value, R, and data for control wells that contained DMSO only are averaged to generate a second control value, $t_{24}$. The effect of each compound tested on dispersion of the biofilm compared to the two control values is calculated thus:

$$\text{If } R < t_0, \text{ then \% Reduction} = \frac{t_0 - R}{t_0};$$

$$\text{and if } R > t_{24}, \text{ then \% Reduction} = \frac{t_{24} - R}{t_{24}}.$$

Table 3 shows the results of this biofilm dispersion screen carried out using the compounds described herein, run against biofilms of the three bacterial species specified in Reference Example 1. Data are expressed in terms of the average percentage reduction of biofilm formed in the presence of each compound, relative to the two control values, for quadruplicate samples. Assays are run as described above, using compound concentrations of 390 μM. Positive numbers indicate dispersion (reduction) of pre-existing biofilms by a compound, and negative numbers indicate enhancement (stimulation of growth) of pre-existing biofilms by a compound (percentage coefficients of variation are ≦15%). This table clearly shows the efficacy of certain compounds in the dispersion of pre-existing biofilms on one or more bacterial species.

TABLE 3

| Cmpd. # | P. aeruginosa | P. fluorescens | S. epidermidis | Structure |
|---|---|---|---|---|
| 7 | −6% | −4% | 0% | 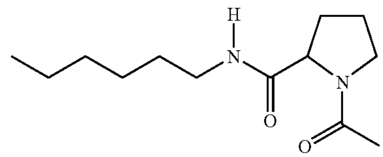 |
| 8 | −30% | −1% | 0% | 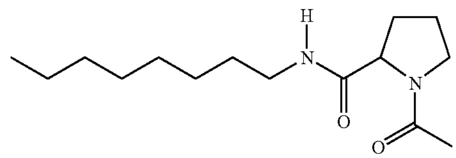 |
| 9 | −68% | −1% | 21% | 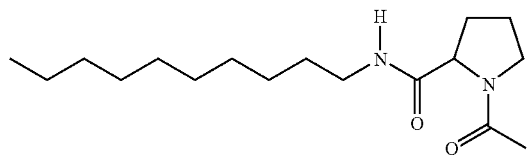 |
| 10 | −9% | −2% | −6% | 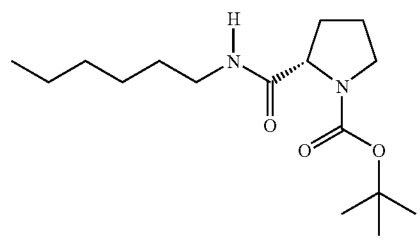 |
| 11 | −56% | −23% | 0% | 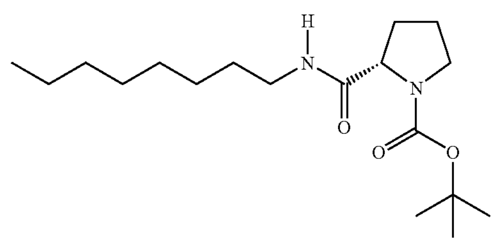 |
| 12 | −30% | −30% | 0% | 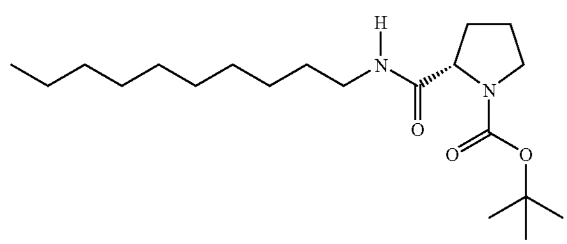 |
| 19 | −25% | 0% | −3% | 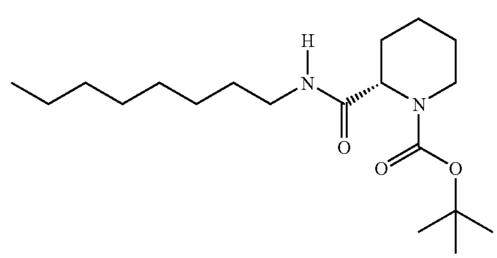 |

TABLE 3-continued
| Cmpd. # | P. aeruginosa | P. fluorescens | S. epidermidis | Structure |
|---|---|---|---|---|
| 20 | 46% | 25% | 0% | 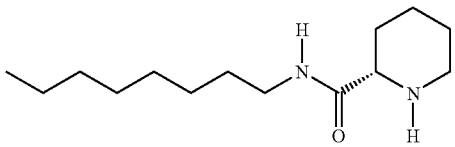 |
| 21 | −39% | −16% | −8% | 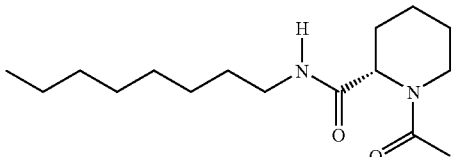 |
| 22 | −54% | 0% | 0% | 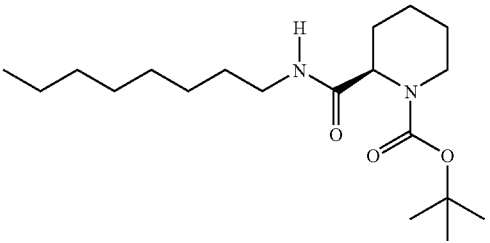 |
| 23 | 0% | 26% | 0% | 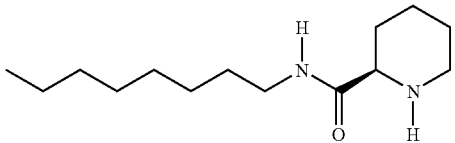 |
| 24 | −17% | 0% | −8% | 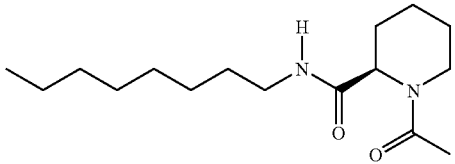 |
| 28 | −25% | 10% | −8% | 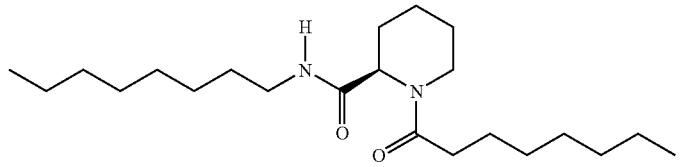 |
| 30 | 1% | 20% | −11% | 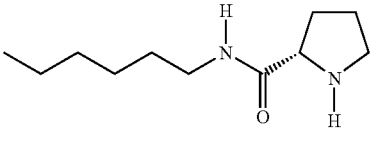 |
| 31 | 21% | 32% | −11% | 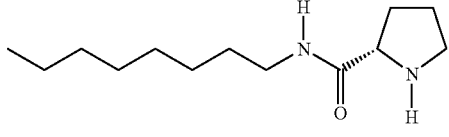 |
| 32 | −107% | 0% | 72% | 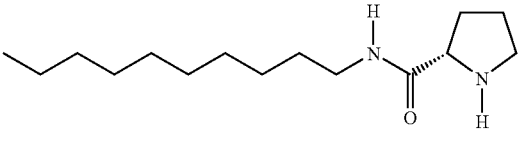 |

TABLE 3-continued
| Cmpd. # | P. aeruginosa | P. fluorescens | S. epidermidis | Structure |
|---|---|---|---|---|
| 152 | −9% | 1% | −4% | 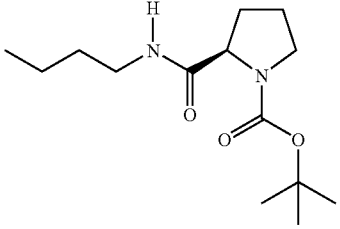 |
| 153 | −7% | 1% | −10% | 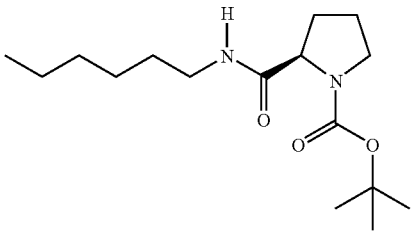 |
| 154 | −63% | 10% | 0% | 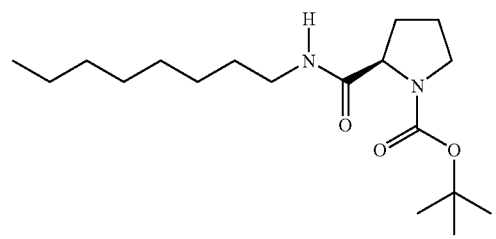 |
| 155 | −12% | 3% | −4% | 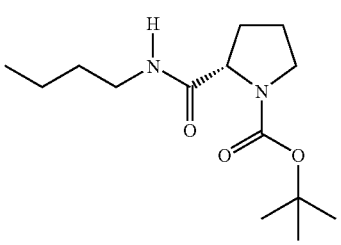 |
| 158 | −53% | −79% | 0% | 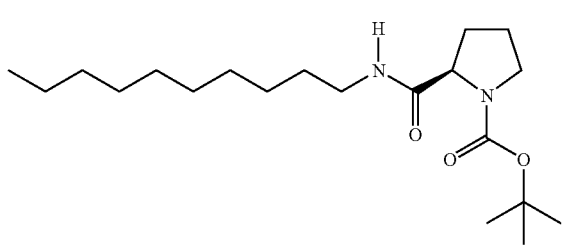 |
| 159 | −55% | −94% | 0% | 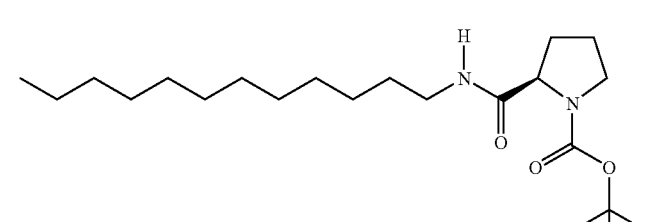 |

TABLE 3-continued
| Cmpd. # | P. aeruginosa | P. fluorescens | S. epidermidis | Structure |
|---|---|---|---|---|
| 160 | −52% | −44% | 0% | 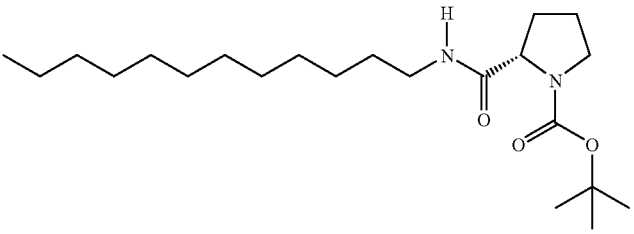 |
| 162 | −23% | 0% | 0% | 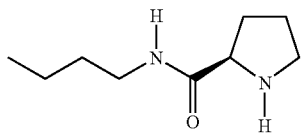 |
| 163 | 4% | 12% | −5% | 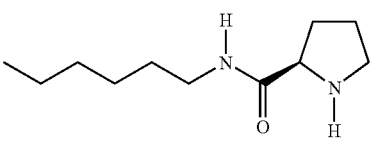 |
| 164 | 38% | 47% | −3% | 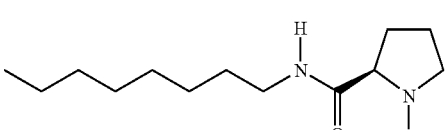 |
| 165 | 0% | 6% | −3% | 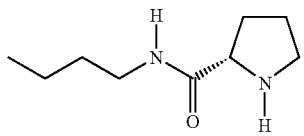 |
| 166 | −2% | 0% | 70% | 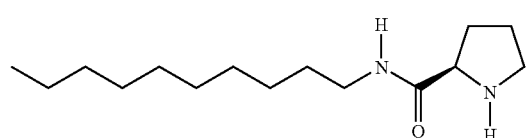 |
| 167 | 4% | 0% | 78% | 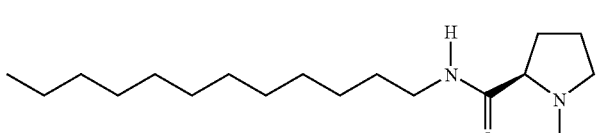 |
| 168 | 17% | −3% | 78% | 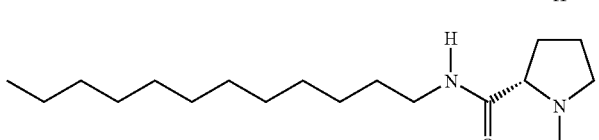 |
| 225 | −23% | −85% | 0% | 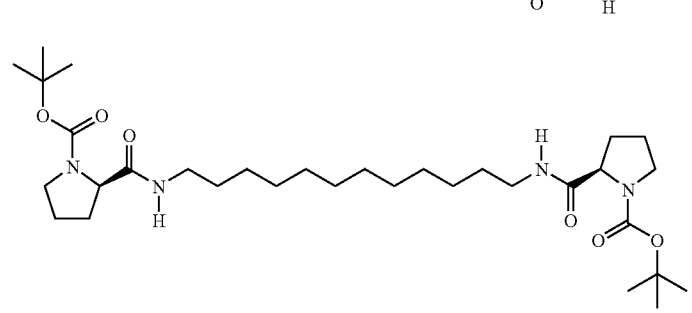 |

TABLE 3-continued
| Cmpd. # | P. aeruginosa | P. fluorescens | S. epidermidis | Structure |
|---|---|---|---|---|
| 226 | 7% | 32% | 26% | 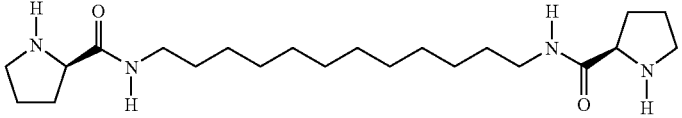 |
| 283 | −11% | 0% | −11% | 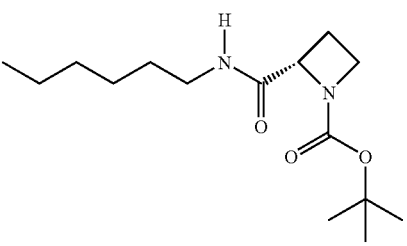 |
| 284 | −79% | −15% | 0% | 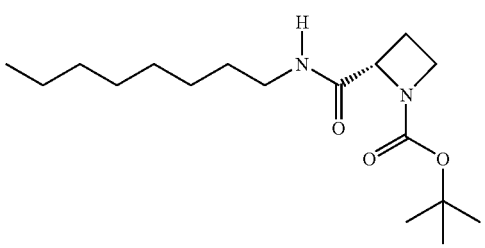 |
| 285 | −37% | −74% | 0% | 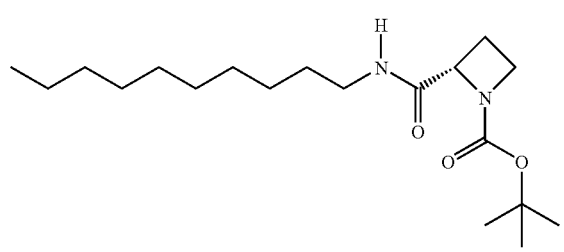 |
| 286 | −83% | −294% | 0% | 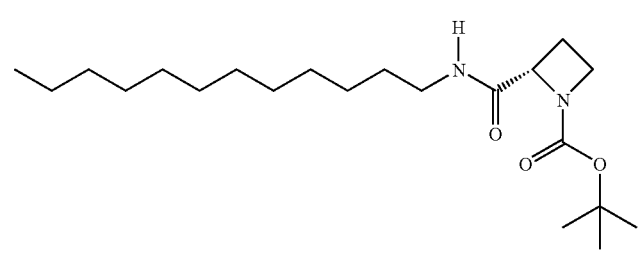 |
| 287 | −70% | −18% | 71% | 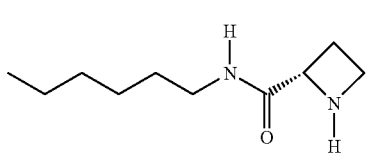 |
| 288 | −32% | −2% | 72% | 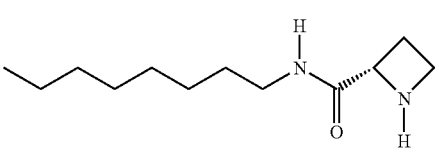 |

TABLE 3-continued

| Cmpd. # | P. aeruginosa | P. fluorescens | S. epidermidis | Structure |
|---|---|---|---|---|
| 289 | −54% | 19% | 84% | 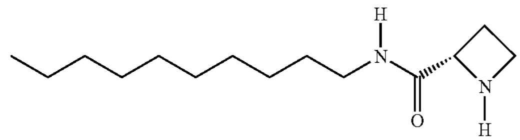 |
| 290 | −72% | 21% | 82% | 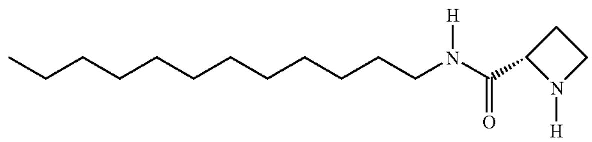 |

Screening Models for Biofilms Grown on Various Hard Surfaces

Quantitative methods for growing model biofilms on any hard surface have been developed, for purposes of testing the efficacy of compounds that control biofilms, such as those discoverable using Reference Example 1. The methods can also be used to determine the susceptibility of bacteria present in biofilms to biocides or other antimicrobials, and to determine the efficacy of compounds that initiate dispersion of biofilms, such as those discoverable using Reference Example 2. Methods to grow and test defined biofilms on surfaces have been previously described (see for example, U.S. Pat. Nos. 6,051,423; 5,605,836; 6,326,190; 2001/0049975; WO0077162; and EP 1038972), however, these methods do not allow for application to many different surfaces, are not amenable to a high-throughput mode, or are not easily made quantitative, or have other features that limit their broad implementation.

This invention relates to methods that can be applied to biofilm growth of almost any bacterium on almost any surface (including polymers, ceramics, metals, glasses, composites, and natural surfaces such as woods), are quantitative, reproducible, and can be made high-throughput. The methods of this invention can also be modified for similar use with fungi such as yeasts, by choosing optimal dyes and growth media. Additionally, the methods of this invention can be used with a consortium of native microbial inocula taken from a biofilm(s) present in a real-world setting or natural environment such as a shower tile surface, toilet bowl surface, skin surface, water pipe, dental or medical waterlines, soil sample, and the like.

Reference Example 4

Biofilm Growth and Test Method Based on Growth in Individual Plastic Vials

Polypropylene 2 ml cryogenic storage vials (Corning #2027) with an internal threaded cap and O-ring are modified by inserting 8 millimeter discs of shower tile, showerstall acrylic plastic, or toilet bowl porcelain into the cavity of the cap. Discs are fixed in place to be flush with the top of the inside cap either by making the diameter slightly larger than the plastic cap, or by first applying a standard silicone adhesive in the cap cavity. The net result is a uniform surface on which a biofilm can be grown, as depicted in FIG. 1.

Modified vials are filled with 0.5–1 mL of modified R2A medium with fructose or pyruvate supplementation (as described in Reference Example 1), and inoculated with 5–10 µL of overnight cultures of P. aeruginosa strain ATCC 10145 or P. fluorescens strain ATCC 13525. Inoculated vials are then placed on a tissue culture rotator (VWR Scientific) at 20–25° C., set at a rotation speed of 1–3 rpm, for 24 hours. Optionally, the 1 mL liquid medium is then replaced with fresh medium, and incubation continues for an additional 24 hours; this sequence of medium replacement and continued growth is done from 1–3 times, to generate biofilms of the desired thickness.

After growth, the vial bottoms are discarded and replaced with fresh vial bottoms that contained 200 µL of a 1% CV solution (in ~10% ethanol). Vials are then re-capped, repositioned on the tissue culture rotator and incubated with the settings described above for 15–75 minutes to stain the biofilms. Vial caps are removed and dipped gently into 4 separate changes of deionized water to remove unbound CV dye, followed by removal of excess water from the cap surfaces. Bound dye on the caps is then extracted by screwing the caps into fresh vial bottoms that contain 0.5–1.0 mL of a solution of 1% sodium deoxycholate in 95% ethanol (and optionally 4–6 glass beads 1–3 mm in diameter to assist dye removal), and vortexing vigorously for 1–5 minutes. Subsequently, either undiluted or diluted (in ethanol) samples of extracted CV are transferred to flat bottom, polystyrene microtiter plates and absorbances at 586 nm are measured in a microplate reader, as described in Reference Example 1.

Table 4 shows the results from replicate vial assays, carried out using 8 millimeter discs fashioned from standard white bathroom tile, using the growth and quantitation conditions specified for P. fluorescens above, with one liquid growth medium replacement after 24 hours of biofilm growth, for a total of 48 hours growth. Data are reported as optical density measured at 586 nm for 200 µL of extracted dye solution, for six replicates. Control vials were not inoculated with bacteria, but were treated exactly as for inoculated vials, and blank data represent microtiter plate wells in the CV quantitation step that contained only buffer. Smaller numbers indicate less biofilm growth. The table indicates that this method results in reproducible data with a good signal to noise ratio relative to controls.

TABLE 4

| Vial # | $OD_{586\ nm}$ |
|---|---|
| 1 | 0.936 |
| 2 | 0.840 |

TABLE 4-continued

| Vial # | OD$_{586\,nm}$ |
|---|---|
| 3 | 0.601 |
| 4 | 0.895 |
| 5 | 0.881 |
| 6 | 0.794 |
| control 1 | 0.076 |
| control 2 | 0.085 |
| blank | 0.038 |
| blank | 0.037 |

Reference Example 5

Biofilm Growth and Test Method Based on 2-Piece Growth-chamber Array

A polypropylene block is machined as indicated in FIGS. 2a, 3, and 4, to generate an array of 24 individual, cylindrical wells that essentially mimic 24 of the cryogenic storage vial bottoms described in Reference Example 4 ('block bottom'). Each well is machined to provide a seat for an O-ring or gasket at the top, and the well-to-well spacing is designed to match that of a standard 96-well microplate, so that a multi-channel pipettor could be used for liquid manipulations. A separate block of polypropylene is machined to provide a recessed lid ('block top') to accommodate a 108×108 millimeter surface (e.g. bathroom tile, porcelain, plastic, glass), as illustrated in FIGS. 2a, 3, and 4. The block bottom contains metal pins to align the block top and bottom, while the block top contains holes drilled to accommodate the pins from the bottom block. The block top also contains set screws to clamp the surface into the recessed holding platform. Additionally, the block bottom contains an adapting arm to allow it to fit onto the motorized portion of a tissue culture rotator. With the surface attached to the top block, the top block is then aligned with the bottom, such that the surface contacts the O-rings or gaskets, which provides a seal to the surface. Threaded holes are machined into both top and bottom blocks to accommodate screws that are used to securely clamp the top and bottom blocks together to provide sufficient pressure on the O-rings to generate the seals. The whole assembly thus accurately mimics 24 of the vial-cap assemblies, as described in Reference Example 3. Optionally, the block design could easily be modified to accommodate other, larger-scale formats (such as 48 or 96-wells).

Wells in the block bottom are filled with 0.5–1 mL of the media described in Reference Example 1, and inoculated with 5–10 μL of overnight cultures of the bacterial strains described in Reference Example 1. The block bottom and top that contain a standard-size, white bathroom tile are then aligned and clamped together, and the assembly placed on a tissue culture rotator (VWR Scientific) set at a rotation speed of 1–3 rpm, or in a shaking incubator, at the appropriate temperature, for 24 hours. Optionally, the 1 mL liquid medium in each well is then replaced with fresh medium, and incubation continued for an additional 24 hours; this sequence of medium replacement and continued growth is done from 1–3 times, to generate biofilms of the desired thickness.

After growth, the block bottom is removed, the liquid is removed and replaced with 200 μL of a 1% CV solution (in ~10% ethanol). The block is then reassembled, re-positioned on the tissue culture rotator and incubated with the settings described above for 15–75 minutes to stain the biofilms. The block pieces are disassembled, and the top block that contains the tile surface is rinsed under a gentle stream of deionized water until all unbound dye is visibly removed. Optionally, any excessive dye adsorbed to the sides of the wells of the block bottom is removed using a test tube brush and a commonly available detergent formulation; this helps to reduce any background due to non-specific staining that can sometimes occur. As a faster alternative, the stained block bottom is simply interchanged with a new or pre-cleaned block bottom. Bound dye on the tile surface is then extracted by pipetting 0.5–1.0 mL of a solution of 1% sodium deoxycholate in 95% ethanol (and optionally 4–6 glass beads 1–3 mm in diameter to assist dye removal) into each well, reassembling the block top and bottom, and either repositioning on the tissue culture rotator followed by incubation using the settings described above for 0.5–2 hours, or alternatively, vortexing vigorously for 1–5 minutes. Subsequently, either undiluted or diluted (in ethanol) samples of extracted CV pipetted from the disassembled blocks are transferred to flat bottom, polystyrene microtiter plates and absorbances are measured in a microplate reader, and compared to controls, as described in Reference Example 1.

After use, the surfaces are removed and discarded, and the wells 80/85 are easily cleaned for re-use by using a test tube brush and commonly available detergent formulations.

It will be obvious to one skilled in the art in light of the present disclosure that the present growth and test method, which is described to test for compounds that prevent biofilm formation, can easily be applied to screening for compounds that initiate dispersion of biofilms, by simply allowing biofilm growth first in the absence of compounds, then measuring the effects of their subsequent addition.

Table 5 shows data collected using the test method described, with biofilm growth of *P. fluorescens* on standard white matte bathroom tile continued for 72 hours, including two exchanges of the liquid growth medium. A polypropylene block top and bottom are used. Data are reported as optical density measured at 586 nm for 200 μL of extracted dye solution, for 16 replicates of inoculated wells, and 8 control well replicates. Control wells (columns 5 and 6) are not inoculated with bacteria, but are treated exactly as for inoculated wells (columns 1 to 4). Smaller numbers indicate less biofilm growth.

TABLE 5

|   | 1 | 2 | 3 | 4 | 5 | 6 |
|---|---|---|---|---|---|---|
| A | 0.442 | 0.444 | 0.576 | 0.566 | 0.302 | 0.331 |
| B | 0.463 | 0.412 | 0.538 | 0.603 | 0.282 | * |
| C | 0.451 | 0.358 | 0.488 | 0.623 | 0.267 | 0.324 |
| D | 0.478 | 0.579 | 0.624 | 0.691 | 0.260 | 0.304 |

* no data obtainable

Table 6 shows similar optical density data, also collected using the test method described, but for biofilm growth of *S. epidermidis* on standard white glossy bathroom tile, for 72 hours, including two exchanges of the liquid growth medium. A polypropylene block top and bottom are used. Data are reported as optical density measurements for 20 replicates of inoculated wells (columns 1 to 5), and 4 control well replicates (column 6). Smaller numbers indicate less biofilm growth.

TABLE 6

|   | 1 | 2 | 3 | 4 | 5 | 6 |
|---|---|---|---|---|---|---|
| A | 0.830 | 0.595 | 1.065 | 1.152 | 1.111 | 0.241 |
| B | 0.633 | 0.858 | 0.849 | 0.878 | 0.743 | * |
| C | 0.842 | 0.746 | 1.561 | 0.822 | 0.801 | 0.167 |
| D | 0.961 | 1.076 | 1.157 | 1.013 | 1.048 | * |

* no data obtainable

Together, Tables 5 and 6 clearly demonstrate that the test method described above yields reproducible biofilm growth for multiple bacterial species, and are suitable for testing of biofilm controlling compound efficacy.

Reference Example 6

Biofilm Growth and Test Method Based on 3-Piece Growth-chamber Array

A polypropylene or TEFLON® block is machined as indicated in FIGS. 2b, 3, and 4, to generate an array of 24 individual, cylindrical wells, as in Reference Example 5, except that the holes are drilled completely through the block. Two lid assemblies are constructed, identical to the lid assembly (block top) described above, and as shown in FIGS. 2b, 3, and 4.

Use of the 3P-GCA is the same as for the 2P-GCA described in Reference Example 5, except that when liquid growth media are being replaced in the wells of the block bottom, only one of the lid assemblies is removed. This arrangement has the advantage that if sensitive biofilms are being investigated, they are not disturbed at all during the entire method. If the biofilms being investigated are not sensitive to disturbance, then an additional advantage of the 3P-GCA is that it can be used to grow biofilms on both surfaces 30 of each lid assembly 90, especially if the 3P-GCA is mounted on a tissue culture rotator for biofilm growth, such that liquid growth media contacts both surfaces 30.

It will be obvious to one skilled in the art in light of the present disclosure that both the 2P-GCA and the 3P-GCA are sufficiently versatile to grow and test biofilms of any bacterium or fungi, on any surface, by optimizing growth media composition and volume, aeration (rotation rate), temperature, media replacement, inoculum size, and other chemical, physical, and biological parameters.

Table 7 shows compounds tested using the 3P-GCA method described above, for biofilm growth of *S. epidermidis* on standard white matte bathroom tile, for 72 hours, including two exchanges of the liquid growth medium. Polypropylene block components are used. Data are reported as optical density measurements for 3 replicates of inoculated wells per compound tested, with 3 inoculated and three uninoculated control well replicates, corresponding to columns 1 (compound 32), 2 (compound 168), 3 (compound 226), 4 (inoculated control), and 5 (uninoculated control). Smaller numbers indicate prevention of biofilm growth.

TABLE 7

|   | 1 | 2 | 3 | 4 | 5 |
|---|---|---|---|---|---|
| A | 0.175 | 1.981 | 0.202 | 2.387 | 0.211 |
| B | 0.244 | 1.581 | 0.269 | 1.870 | 0.162 |
| C | 0.207 | 1.517 | 0.147 | 2.201 | 0.206 |

From this data, compounds 32 and 226 clearly have a strong biofilm prevention activity, whereas compound 168 has a much more modest effect in this test method, the method being significantly more realistic but lower throughput that the methods described in Reference Examples 1 and 2.

It will be obvious to one skilled in the art in light of the present disclosure that the present growth and test method, which is described to test for compounds that prevent biofilm formation, can easily be applied to screening for compounds that initiate dispersion of biofilms, by simply allowing biofilm growth first in the absence of compounds, then measuring the effects of their subsequent addition.

While particular embodiments of the present invention have been illustrated and described, it would be obvious to those skilled in the art in light of the present disclosure that various other changes and modifications can be made without departing from the spirit and scope of the invention. It is therefore intended to cover in the appended claims all such changes and modifications that are within the scope of this invention.

What is claimed is:

1. A compound of formula A wherein n is 1; and
R and $R_1$ are H;
$R_2$ is $C_6$–$C_{12}$ alkyl.

2. A composition comprising an effective amount for preventing biofilm formation or dispersing an existing bioflim comprising a compound of claim 1 and an inert carrier.

3. A method of preventing bioflim formation or dispersing an existing biofilm, comprising contacting the substrate surface with a compound having formula A wherein n is 1; and
R and $R_1$ are H;
$R_2$ is $C_6$–$C_{12}$ alkyl.

4. The method of claim 2 wherein R is H, $R_1$ is H, and $R_2$ is $C_{10}$ alkyl.

* * * * *

UNITED STATES PATENT AND TRADEMARK OFFICE
CERTIFICATE OF CORRECTION

PATENT NO. : 7,018,642 B2
APPLICATION NO. : 10/132906
DATED : March 28, 2006
INVENTOR(S) : Charles Raymond Degenhardt et al.

It is certified that error appears in the above-identified patent and that said Letters Patent is hereby corrected as shown below:

Col. 20, line 60, to Col. 21, line 10, delete

"

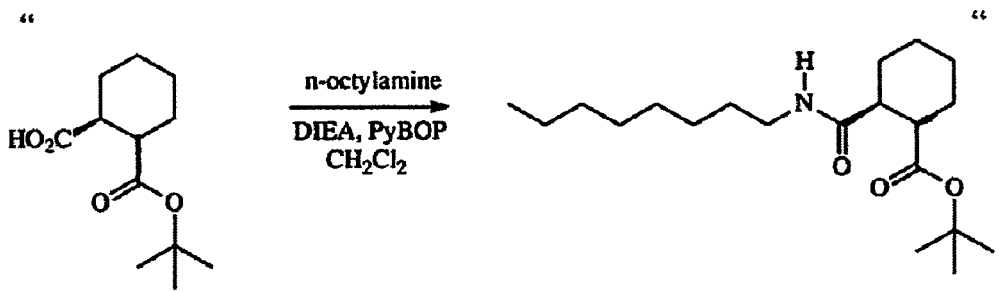

and insert

--

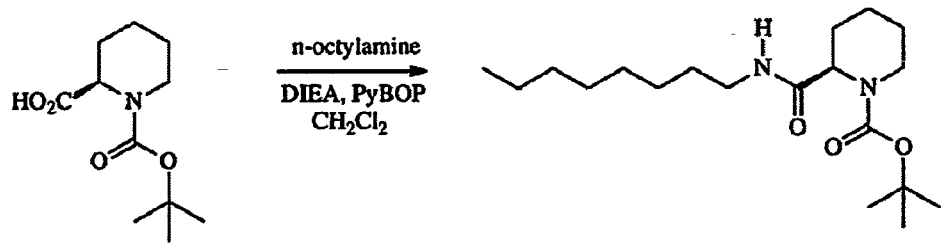

--.

UNITED STATES PATENT AND TRADEMARK OFFICE
CERTIFICATE OF CORRECTION

PATENT NO. : 7,018,642 B2  Page 2 of 2
APPLICATION NO. : 10/132906
DATED : March 28, 2006
INVENTOR(S) : Charles Raymond Degenhardt et al.

It is certified that error appears in the above-identified patent and that said Letters Patent is hereby corrected as shown below:

Col. 21, line 40, delete "

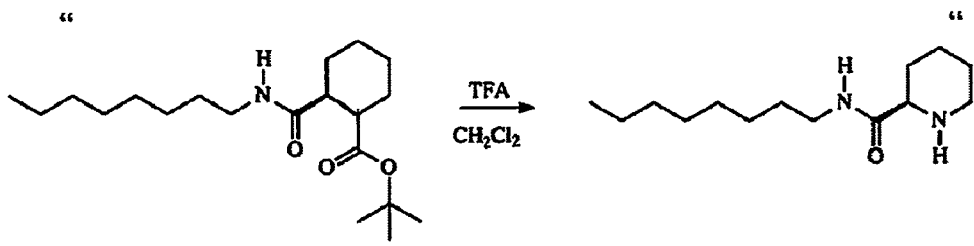

and insert

--

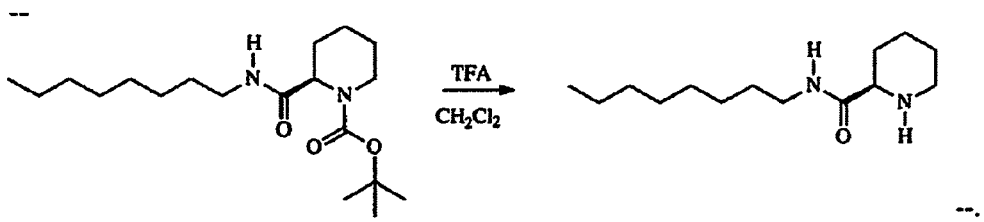

--.

Column 64, line 61, delete "2" and insert --3--.

Signed and Sealed this

Twenty-eighth Day of November, 2006

JON W. DUDAS
*Director of the United States Patent and Trademark Office*